United States Patent
Belmonte et al.

(10) Patent No.: US 11,583,549 B2
(45) Date of Patent: Feb. 21, 2023

(54) HIGH ELASTICITY HYALURONAN COMPOSITIONS AND METHODS OF USE THEREOF

(71) Applicant: Matrix Biology Institute, Edgewater, NJ (US)

(72) Inventors: Carlos Belmonte, San Juan de Alicante (ES); Janet L. Denlinger, Edgewater, NJ (US)

(73) Assignee: Matrix Biology Institute, Edgewater, NJ (US)

( * ) Notice: Subject to any disclaimer, the term of this patent is extended or adjusted under 35 U.S.C. 154(b) by 0 days.

(21) Appl. No.: 17/115,242

(22) Filed: Dec. 8, 2020

(65) Prior Publication Data

US 2021/0085709 A1    Mar. 25, 2021

Related U.S. Application Data

(63) Continuation of application No. 16/460,557, filed on Jul. 2, 2019, now Pat. No. 10,888,580, which is a continuation of application No. 15/271,434, filed on Sep. 21, 2016, now Pat. No. 10,383,889.

(60) Provisional application No. 62/232,364, filed on Sep. 24, 2015.

(51) Int. Cl.
*A61K 31/728* (2006.01)
*A61K 9/00* (2006.01)
*A61K 47/02* (2006.01)

(52) U.S. Cl.
CPC .......... *A61K 31/728* (2013.01); *A61K 9/0014* (2013.01); *A61K 9/0019* (2013.01); *A61K 9/0048* (2013.01); *A61K 47/02* (2013.01)

(58) Field of Classification Search
None
See application file for complete search history.

(56) References Cited

U.S. PATENT DOCUMENTS

| | | |
|---|---|---|
| 4,141,973 A | 2/1979 | Balazs |
| 4,957,744 A | 9/1990 | della Valle et al. |
| 5,234,914 A | 8/1993 | Gallina |
| 5,679,655 A | 10/1997 | Gallina |
| 6,953,776 B2 | 10/2005 | Di Napoli |
| 7,544,671 B2 | 6/2009 | Karageozian et al. |
| 7,674,781 B2 | 3/2010 | Sheardown et al. |
| 7,863,256 B2 | 1/2011 | Schiavinato et al. |
| 7,943,596 B2 | 5/2011 | Ueno et al. |
| 8,093,365 B2 | 1/2012 | Wisniewski et al. |
| 8,153,614 B2 | 4/2012 | Asari |
| 8,323,617 B2 | 12/2012 | Gooding et al. |
| 8,329,746 B2 | 12/2012 | Waddell |
| 8,338,388 B2 | 12/2012 | Lebreton |
| 8,377,468 B2 | 2/2013 | Goodheart |
| 8,388,995 B1 | 3/2013 | Ali et al. |
| 8,398,611 B2 | 3/2013 | Hwang et al. |
| 8,455,436 B2 | 6/2013 | Byers et al. |
| 8,524,662 B2 | 9/2013 | Byers et al. |
| 8,529,938 B2 | 9/2013 | Jafari et al. |
| 8,563,532 B2 | 10/2013 | Lebreton |
| 9,012,517 B2 | 4/2015 | Guillen et al. |
| 9,044,425 B2 | 6/2015 | Babizhayev |
| 9,492,474 B2 | 11/2016 | Balazs et al. |
| 10,383,889 B2 | 8/2019 | Belmonte et al. |
| 10,383,890 B2 | 8/2019 | Balazs et al. |
| 10,888,580 B2 | 1/2021 | Belmonte et al. |
| 10,933,085 B2 | 3/2021 | Balazs et al. |
| 2001/0041671 A1 | 11/2001 | Napoli |
| 2003/0133986 A1 | 7/2003 | Tsao |
| 2004/0022847 A1 | 2/2004 | Leneau |
| 2004/0167480 A1 | 8/2004 | Bos |
| 2005/0059639 A1 | 3/2005 | Wei |
| 2006/0094643 A1 | 5/2006 | Svirkin et al. |
| 2006/0183698 A1 | 8/2006 | Abelson |
| 2007/0254841 A1 | 11/2007 | Ousler et al. |
| 2007/0293648 A1 | 12/2007 | Sheardown et al. |
| 2008/0050335 A1 | 2/2008 | Faour et al. |
| 2009/0111770 A1 | 4/2009 | Holzer et al. |
| 2010/0048755 A1 | 2/2010 | Chow et al. |
| 2010/0074957 A1 | 3/2010 | Robinson et al. |
| 2010/0178317 A1 | 7/2010 | Burke et al. |
| 2010/0184720 A1 | 7/2010 | Gavard Molliard et al. |
| 2010/0303915 A1 | 12/2010 | Yu |
| 2011/0066138 A1 | 3/2011 | Fezza |
| 2011/0071631 A1 | 3/2011 | Rosenthal |

(Continued)

FOREIGN PATENT DOCUMENTS

| AU | 2320888 A | 3/1989 |
|---|---|---|
| EP | 0138572 A2 | 4/1985 |

(Continued)

OTHER PUBLICATIONS

[No Author Listed], Design and conduct of clinical trials: report of the Clinical Trials Subcommittee of the International Dry Eye Workshop (2007). Ocul Surf. Apr. 2007;5(2):153-62.

[No Author Listed], Management and therapy of dry eye disease: report of the Management and Therapy Subcommittee of the International Dry Eye Workshop (2007). Ocul Surf. Apr. 2007;5(2):163-78.

[No Author Listed], Methodologies to diagnose and monitor dry eye disease: report of the Diagnostic Methodology Subcommittee of the International Dry Eye Workshop (2007). Ocul Surf. Apr. 2007;5(2):108-52.

[No Author Listed], Research in dry eye: report of the Research Subcommittee of the International Dry Eye Workshop (2007). Ocul Surf. Apr. 2007;5(2):179-93.

(Continued)

*Primary Examiner* — Dale R Miller
(74) *Attorney, Agent, or Firm* — McCarter & English, LLP; Maria Laccotripe Zacharakis; Yelena Margolin

(57) ABSTRACT

The present invention provides methods for alleviating pain and discomfort associated with a dry eye condition; methods for alleviating pain and discomfort while minimizing at least one skin imperfection; and methods for alleviating pain and discomfort while facilitating wound healing. The methods involve administering to a subject in need thereof a composition comprising hyaluronan with high elasticity.

16 Claims, 1 Drawing Sheet

(56) References Cited

U.S. PATENT DOCUMENTS

| | | | |
|---|---|---|---|
| 2011/0171310 A1 | 7/2011 | Gousse et al. |
| 2011/0201571 A1 | 8/2011 | Gavard Molliard |
| 2012/0128754 A1 | 5/2012 | Wei |
| 2012/0165257 A1 | 6/2012 | Byers et al. |
| 2012/0258931 A1 | 10/2012 | Bailleul |
| 2012/0264689 A1 | 10/2012 | Mize |
| 2013/0172287 A1 | 7/2013 | Shichijo et al. |
| 2013/0195952 A1 | 8/2013 | Byrne et al. |
| 2013/0209531 A1 | 8/2013 | Prestwich et al. |
| 2013/0296264 A1 | 11/2013 | Davis et al. |
| 2013/0303695 A1 | 11/2013 | Sheardown et al. |
| 2014/0005140 A1 | 1/2014 | Piron et al. |
| 2014/0088037 A1 | 3/2014 | Bon Betemps et al. |
| 2014/0221309 A1 | 8/2014 | Beard et al. |
| 2015/0018305 A1 | 1/2015 | Asari et al. |
| 2015/0037422 A1 | 2/2015 | Kaplan et al. |
| 2015/0148310 A1 | 5/2015 | Prestwich |
| 2015/0151858 A1 | 6/2015 | Turzi |
| 2015/0173951 A1 | 6/2015 | Fezza |
| 2015/0209385 A1 | 7/2015 | Prestwich et al. |

FOREIGN PATENT DOCUMENTS

| | | | |
|---|---|---|---|
| EP | 0414373 A2 | 2/1991 |
| EP | 0499164 A1 | 8/1992 |
| EP | 0781547 A1 | 7/1997 |
| EP | 1908457 A1 | 4/2008 |
| EP | 2596796 A1 | 5/2013 |
| EP | 2614838 A1 | 7/2013 |
| EP | 2979539 A1 | 2/2016 |
| JP | 2003-119147 A | 4/2003 |
| JP | 2009-196903 A | 9/2009 |
| JP | 2010-531863 A | 9/2010 |
| JP | 2012-62269 A | 3/2012 |
| JP | 2012-514579 A | 6/2012 |
| JP | 2013-035860 A | 2/2013 |
| JP | 2015-526489 A | 9/2015 |
| RU | 2126669 C1 | 2/1999 |
| WO | WO-1989/01777 A1 | 3/1989 |
| WO | WO-1998/39015 A1 | 9/1998 |
| WO | WO-2007/059890 A1 | 5/2007 |
| WO | WO-2011/044367 A1 | 4/2011 |
| WO | WO-2012/143876 A1 | 10/2012 |
| WO | WO-2013/186493 A2 | 12/2013 |
| WO | WO-2014/032804 A1 | 3/2014 |
| WO | WO-2014/152328 A1 | 9/2014 |
| WO | WO-2014/156939 A1 | 10/2014 |
| WO | WO-2014/191955 A1 | 12/2014 |
| WO | 2015/006460 A1 | 1/2015 |
| WO | WO-2015/074137 A1 | 5/2015 |
| WO | WO-2015/097261 A1 | 7/2015 |

OTHER PUBLICATIONS

[No Author Listed], Sodium Hyaluronate Ophthalmic Solution 0.18% for the Treatment of the Signs and Symptoms of Dry Eye Disease. Dermatologic and Ophthalmic Drugs Advisory Committee Meeting Briefing Document, NDA 22-359 FDA Advisory Committee Briefing Document, 116 pages, Jun. 2009.

[No Author Listed], The definition and classification of dry eye disease: report of the Definition and Classification Subcommittee of the International Dry Eye Workshop (2007). Ocul Surf. Apr. 2007;5(2):75-92.

[No Author Listed], The epidemiology of dry eye disease: report of the Epidemiology Subcommittee of the International Dry Eye Workshop (2007). Ocul Surf. Apr. 2007;5(2):93-107.

Acosta et al., Corneal sensory nerve activity in an experimental model of UV keratitis. Invest Ophthalmol Vis Sci. May 1, 2014;55(6):3403-12.

Acosta et al., Sensory experiences in humans and single-unit activity in cats evoked by polymodal stimulation of the cornea. J Physiol. Jul. 15, 2001;534(Pt. 2):511-25.

Acosta et al., The influence of eye solutions on blinking and ocular comfort at rest and during work at video display terminals. Exp Eye Res. Jun. 1999;68(6):663-9.

Advanced BioMatrix, Hyaluronan Gels, Catalog #5011,5012, 5013 and 5014. http://www.advancedbiomatrix.com. 2 pages. May 24, 2011.

Advanced BioMatrix. Innovative 3D Matrix Products for Scientific Research. Retrieved online at: https://www.advancedbiomatrix.com. 16 pages, last accessed Dec. 3, 2015.

Ahn et al., Clinical comparison of two hyaluronic acid-derived fillers in the treatment of nasolabial folds: Mesoglow® and IAL System®. Int J Dermatol. May 2012;51(5):601-8.

Alves et al., Dry eye disease treatment: a systematic review of published trials and a critical appraisal of therapeutic strategies. Ocul Surf. Jul. 2013;11(3):181-92.

Aragona et al., Long term treatment with sodium hyaluronate-containing artificial tears reduces ocular surface damage in patients with dry eye. Br J Ophthalmol. Feb. 2002;86(2):181-4.

Aragona et al., Sodium hyaluronate eye drops of different osmolarity for the treatment of dry eye in Sjögren's syndrome patients. Br J Ophthalmol. Aug. 2002;86(8):879-84.

Arshinoff et al., HsS versus a balanced salt solution as a corneal wetting agent during routine cataract extraction and lens implantation. J Cataract Refract Surg. Oct. 1997;23(8):1221-5.

Balazs et al., iscosupplementation: a new concept in the treatment of osteoarthritis. J Rheumatol Suppl. Aug. 1993;39:3-9.

Balazs, Viscosupplementation for the Treatment of Osteoarthritis: From Initial Discovery to Current Status and Results. Surgical Technology International XII. Dec. 31, 2003;12;278-89.

Belmonte et al., Modulation by hyaluronan and its derivatives (hylans) of sensory nerve activity signalling articular pain. The Chemistry, Biology and Medical Applications of Hyaluronan and its Derivatives. 1998(72):205-17.

Berenbaum et al., A randomised, double-blind, controlled trial comparing two intra-articular hyaluronic acid preprations differing by their molecular weight in symptomatic knee osteoarthritis. Ann Rheum Dis. 2012;71(9):1454-60.

Bhuanantanondh et al., Rheological Study of Viscosupplements and Synovial Fluid in Patients with Osteoarthritis. J Med Biol Eng. 2010;32(1):12-6.

Biomatrix, Inc., Hylashield® CL Lubricating Eye Drop hylan fluid, 0.15% Lubricant—Wetting/Rewetting Drop. 510(k) Summary. 8 pages, Mar. 2, 2000.

Boettger et al., Evaluation of long-term antinociceptive properties of stabilized hyaluronic acid preparation (NASHA) in an animal model of repetitive joint pain. Arthritis Res Ther. Jul. 7, 2011;13(4):R110.

Borzacchiello et al., Effect of hyaluronic acid amide derivative on equine synovial fluid viscoelasticity. J Biomed Mater Res A. Mar. 1, 2010;92(3):1162-70.

Bothner et al., Rheology of hyaluronate. Acta Otolaryngol Suppl. 1987;442:25-30.

Brjesky et al., Use of preservative-free hyaluronic acid (Hylabak(®)) for a range of patients with dry eye syndrome: experience in Russia. Clin Ophthalmol. Jun. 18, 2014;8:1169-77.

Bron et al., Rethinking dry eye disease: a perspective on clinical implications. Ocul Surf. Apr. 2014;12(2 Suppl):S1-31.

Cheema et al., Sodium hyaluronate eye drops in the treatment of dry eye disease: an open label, uncontrolled, multi-centre trial. J Ayub Med Coll Abbottabad. Dec.-Jul. 2012;24(3-4):14-6.

Colligris et al., Recent developments on dry eye disease treatment compounds. Saudi J Ophthalmol. Jan. 2014;28(1):19-30.

Cowman et al., Experimental approaches to hyaluronan structure. Carbohydr Res. Apr. 11, 2005;340(5):791-809.

Cowman et al., Macromolecular Crowding in the Biomatrix. Structure and Function of Biomatrix: Control of Cell Behavior and Gene Expression. E.A. Balazs (Ed.), Matrix Biology Institute. pp. 45-66, (2012).

Craig, Dry Eye Part 2: Current therapeutic and management options. Bausch & Lomb Academy of Vision Care, www.academyofvisioncare.com. 11 pages, (2009).

De Smedt et al., Viscoelastic and transient network properties of hyaluronic acid as a function of the concentration. Biorheology. Jan.-Feb. 1993;30(1):31-41.

(56) References Cited

OTHER PUBLICATIONS

Deluise et al., The use of topical Healon tears in the management of refractory dry-eye syndrome. Ann Ophthalmol. Sep. 1984;16(9):823-4.
Dumbleton et al., An investigation of the efficacy of a novel ocular lubricant. Eye Contact Lens. May 2009;35(3):149-55.
Falcone et al., Rheological and cohesive properties of hyaluronic acid. J Biomed Mater Res A. Mar. 15, 2006;76(4):721-8.
Fam et al., Effect of concentration and molecular weight on the rheology of hyaluronic acid/bovine calf serum solutions. Biorheology. 2009;46(1):31-43.
Finelli et al., A new viscosupplement based on partially hydrophobic hyaluronic acid: a comparative study. Biorheology. 2011;48(5):263-75.
Gomis et al., Effects of different molecular weight elastoviscous hyaluronan solutions on articular nociceptive afferents. Arthritis Rheum. Jan. 2004;50(1):314-26.
Gomis et al., Hyaluronan Derivatives and Joint Pain. Hyaluronan: Structure, Metabolism, Biological Activities, Therapeutic Applications, 1st Edition. vol. II Balazs, EA (Ed.). Matrix Biology Institute, Edgewater, NJ 07020 (USA), pp. 503-507, (2005).
Gomis et al., Intra-articular injections of hyaluronan solutions of different elastoviscosity reduce nociceptive nerve activity in a model of osteoarthritic knee joint of the guinea pig. Osteoarthritis Cartilage. Jun. 2009;17(6):798-804.
Gomis et al., Nociceptive nerve activity in an experimental model of knee joint osteoarthritis of the guinea pig: effect of intra-articular hyaluronan application. Pain. Jul. 2007;130(1-2):126-36.
Gotoh et al., Effects of the molecular weight of hyaluronic acid and its action mechanisms on experimental joint pain in rats. Annals of the Rheumatic Diseases. 1993;52:817-22.
Gotoh et al., Experimental knee pain model in rats and analgesic effect of sodium hyaluronate (SPH). Nihon Yakurigaku Zasshi. Jul. 1988;92(1):17-27.
Graue et al., The protective effect of Na-hyaluronate to corneal endothelium. Exp Eye Res. Jul. 1980;31(1):119-27.
Guillaumie et al., Comparative studies of various hyaluronic acids produced by microbial fermentation for potenital topical ophthalmic applications. Journal of Biomedical Materials Research Part A. 2010;92A:1421-30.
Hamano et al., Evaluation of the effect of the sodium hyaluronate ophthalmic solution on tear film stability-non-contact specular microscopic evaluation. Nippon Ganka Gakkai Zasshi. Aug. 1993;97(8):928-32.
Hoare et al., Rheological blends for drug delivery. II. Prolongation of nerve blockade, biocompatibility, and in vitro-in vivo correlations. J Biomed Mater Res A. Feb. 2010;92(2):586-95.
Horkay et al., Ions in hyaluronic acid solutions. J Chem Phys. Nov. 14, 2009;131(18):184902. 8 pages.
Iannitti et al., A new highly viscoelastic hyaluronic acid gel: rheological properties, biocompatibility and clinical investigation in esthetic and restorative surgery. Int J Pharm. Nov. 18, 2013;456(2):583-92.
Iannitti et al., Preliminary histopathological study of intra-articular injection of a novel highly cross-linked hyaluronic acid in a rabbit model of knee osteoarthritis. J Mol Histol. Apr. 2013;44(2):191-201.
Ibrahim et al., The impact of hyaluronic acid oligomer content on physical, mechanical, and biologic properties of divinyl sulfone-crosslinked hyaluronic acid hydrogels. J Biomed Mater Res A. Aug. 2010;94(2):355-70.
Iester et al., Improvement of the ocular surface using hypotonic 0.4% hyaluronic acid drops in keratoconjunctivitis sicca. Eye (bond). Dec. 2000;14(Pt 6):892-8.
Johnson et al., Effectiveness of sodium hyaluronate eyedrops in the treatment of dry eye. Graefes Arch Clin Exp Ophthalmol. Jan. 2006;244(1):109-12.
Kamiya et al., Clinical evaluation of the additive effect of diquafosol tetrasodium on sodium hyaluronate monotherapy in patients with dry eye syndrome: a prospective, randomized, multicenter study. Eye (Lond). Oct. 2012;26(10):1363-8.
Kerr et al., Surface rheological properties of hyaluronic acid solutions. Biorheology. 1985;22(2):133-44.
Kiss et al., Isotonic Glycerol and Sodium Hyaluronate Containing Artificial Tear Decreases Conjunctivochalasis after One and Three Months: A Self-Controlled, Unmasked Study. PLoS One. Jul. 14, 2015;10(7):e0132656. 13 pages.
Kobayashi et al., Viscoelasticity of hyaluronic acid with different molecular weights. Biorheology. May-Jun. 1994;31(3):235-44.
Kogan et al., Hyaluronic acid: a natural biopolymer with a broad range of biomedical and industrial applications. Biotechnol Lett. Jan. 2007;29(1):17-25.
Krause et al., Rheology of sodium hyaluronate under physiological conditions. Biomacromolecules. 2001 Spring;2(1):65-9.
Larsen et al., Biocompatibility of Hylan Polymers in Various Tissue Compartments. Mat Res Soc Symp Proc. 1995;394:149-53.
Larsen et al., Hylashield (2.0 Pa Elastoviscous Hylan Fluid 0.15%) Protective Corneal Shield: Evaluation of Biological and Physical Properties. Ophthalmic Practice. Jun. 1994;12(3):137-40.
Lee et al., Comparison of cytotoxicity and wound healing effect of carboxymethylcellulose and hyaluronic acid on human corneal epithelial cells. Int J Ophthalmol. Apr. 18, 2015;8(2):215-21.
Lee et al., Efficacy of sodium hyaluronate and carboxymethylcellulose in treating mild to moderate dry eye disease. Cornea. Feb. 2011;30(2):175-9.
Li et al., Effects of eye drops containing a mixture of omega-3 essential fatty acids and hyaluronic acid on the ocular surface in desiccating stress-induced murine dry eye. Curr Eye Res. Sep. 2014;39(9):871-8.
Lin et al., Dry eye disease: A review of diagnostic approaches and treatments. Saudi J Ophthalmol. Jul. 2014;28(3):173-81.
Lopez-Garcia et al., Autologous serum eye drops diluted with sodium hyaluronate: clinical and experimental comparative study. Acta Ophthalmol. Feb. 2014;92(1):e22-9.
Lundsgaard et al., Intra-articular sodium hyaluronate 2 mL versus physiological saline 20 mL versus physiological saline 2 mL for painful knee osteoarthritis: a randomized clinical trial. Scand J Rheumatol. Mar.-Apr. 2008;37(2):142-50.
Madrid et al., Contribution of TRPM8 channels to cold transduction in primary sensory neurons and peripheral nerve terminals. J Neurosci. Nov. 29, 2006;26(48):12512-25.
Matsuo, Trehalose versus hyaluronan or cellulose in eyedrops for the treatment of dry eye. Jpn J Ophthalmol. Jul.-Aug. 2004;48(4):321-7.
Matteini et al., Structural behavior of highly concentrated hyaluronan. Biomacromolecules. Jun. 8, 2009;10(6):1516-22.
Maulvi et al., Extended release of hyaluronic acid from hydrogel contact lenses for dry eye syndrome. J Biomater Sci Polym Ed. 2015;26(15):1035-50.
McDonald et al., A randomised, crossover, multicentre study to compare the performance of 0.1% (w/v) sodium hyaluronate with 1.4% (w/v) polyvinyl alcohol in the alleviation of symptoms associated with dry eye syndrome. Eye (Lond). Sep. 2002;16(5):601-7.
Mo et al., Effects of sodium chloride, Guanidine Hychrorid, and Sucrose on the Viscoelastic Properties of Sodium Hyaluronate Solutions. Biopolymers. 1999;50:23-34.
Moshirfar et al., Artificial tears potpourri: a literature review. Clin Ophthalmol. Jul. 31, 2014;8:1419-33.
Nepp et al., The clinical use of viscoelastic artificial tears and sodium chloride in dry-eye syndrome. Biomaterials. Dec. 2001;22(24):3305-10.
Oka et al., Effects of High Molecular Weight Hyaluronate on the Lubrication Mechanism of the Joint. Journal of Japanese Society for Rheumatism Joint Surgery. 1993;XII(3):259-66.
Papa et al., Comparison of hypotonic and isotonic solutions containing sodium hyaluronate on the symptomatic treatment of dry eye patients. Ophthalmologica. Mar.-Apr. 2001;215(2):124-7.
Parra et al., Ocular surface wetness is regulated by TRPM8-dependent cold thermoreceptors of the cornea. Nat Med. Dec. 2010;16(12):1396-9.

(56) References Cited

OTHER PUBLICATIONS

Pauloin et al., High molecular weight hyaluronan decreases UVB-induced apoptosis and inflammation in human epithelial corneal cells. Mol Vis. 2009;15:577-83.
Pauloin et al., In vitro modulation of preservative toxicity: high molecular weight hyaluronan decreases apoptosis and oxidative stress induced by benzalkonium chloride. Eur J Pharm Sci. Aug. 7, 2008;34(4-5):263-73.
Pena Ede et al., Elastoviscous substances with analgesic effects on joint pain reduce stretch-activated ion channel activity in vitro. Pain. Oct. 2002;99(3):501-8.
Polack et al., Sodium hyaluronate (Healon) in keratoplasty and IOL implantation. Ophthalmology. May 1981;88(5):425-31.
Polack et al., The Treatment of Dry Eyes with Na Hyaluronate (Healon®), A Preliminary Report. Cornea. 1982;1:133-6.
Polack, Penetrating keratoplasty using MK stored corneas and Na Hyaluronate (Healon). Trans Am Ophthalmol Soc. 1982;80:248-61.
Pozo et al., Reduction of sensory responses to passive movements of inflamed knee joints by hylan, a hyaluronan derivative. Exp Brain Res. Aug. 1997;116(1):3-9.
Product Description for Acquafiller Dermal Filler Hylauronic Acid Fine Wrinkles 35mg/ml + Lidocaine 2%-2ml, available at http://acquafiller.com/acquafiller-dermal-filler-hyaluronic-acid-fine-wrinkles-35mg-ml-lidocaine-2-2ml.html, last accessed Nov. 24, 2015.
Product Description for Acquafiller Dermal Filler Hylauronic Acid Fine Wrinkles 45mg/ml + Lidocaine 2%-2ml, available at http://acquafiller.com/acquafiller-dermal-filler-hyaluronic-acid-fine-wrinkles-45mg-ml-lidocaine-2-2ml.html, last accessed Dec. 1, 2015.
Product Description for Acquafiller Dermal Filler Hylauronic Acid Plus 45mg/ml + Lidocaine 2%-2ml, available at http://acquafiller.com/acquafiller-dermal-filler-hyaluronic-acid-plus-45mg-ml-lidocaine-2-2ml.html, last accessed Dec. 1, 2015.
Rah, A review of hyaluronan and its ophthalmic applications. Optometry. Jan. 2011;82(1):38-43.
Saeed et al., Effectiveness of sodium hyaluronate eye gel in patients with dry eye disease: a multi-centre, open label, uncontrolled study. Pak J Med Sci. Jul. 2013;29(4):1055-8.
Santoro et al., Rheological properties of cross-linked hyaluronic acid dermal fillers. J Appl Biomater Biomech. May-Aug. 2011;9(2):127-36.
Schiraldi et al., Biotechnological Production and Application of Hyaluronan. Biopolymers, Biotechnological Production and Application of Hyaluronan. Magby Elnashar (Ed.). InTech. Chapter 20, pp. 387-412, (2010).
Shimmura et al., Sodium hyaluronate eyedrops in the treatment of dry eyes. Br J Ophthalmol. Nov. 1995;79(11):1007-11.
Simmons et al., Efficacy and safety of two new formulations of artificial tears in subject with dry eye disease: a 3-month, multi-center, active-controlled, randomized trial. Clinical Ophthalmology. 2015;9:665-75.
Snibson et al., Precorneal residence times of sodium hyaluronate solutions studied by quantitative gamma scintigraphy. Eye (Lond). 1990;4 ( Pt 4):594-602.
Stuart et al., Dilute sodium hyaluronate (Healon) in the treatment of ocular surface disorders. Ann Ophthalmol. Mar. 1985;17(3):190-2.
Tanaka, The Effect of High-molecular-weight Hyaluronic Acid on Osteoarthritis of the Knee. Journal of Japanese Society for Rheumatism Joint Surgery. 2006;XXV(2):103-11.
Tasciotaoglu et al., Efficacy of intra-articular sodium hyaluronate in the treatment of knee osteoarthritis. Clin Rheumatol. May 2003;22(2):112-7.
Teping et al., Drug Report, Hyaluronic acid, Treatment of Sicca Syndrome—Effective and well-tolerated also with contact lenses. Klinische Monatsblatter fur die Augenheilkunde Feb. 2010;4(227):1-13.
Tong et al., Choice of artificial tear formulation for patients with dry eye: where do we start? Cornea. Nov. 2012;31 Suppl 1:S32-6.
Troiano et al., Effect of hypotonic 0.4% hyaluronic acid drops in dry eye patients: a cross-over study. Cornea. Dec. 2008;27(10):1126-30.
Vogel et al., Demonstration of efficacy in the treatment of dry eye disease with 0.18% sodium hyaluronate ophthalmic solution (vismed, rejena). Am J Ophthalmol. Apr. 2010;149(4):594-601.
Wada, Hyaluronan Chemistry for Application. Sen'i Gakkaishi. 2009;65(11):p. 407-p. 411.
Weiss et al., Basic Principles Underlying the Development of Viscosupplementation for the Treatment of Osteoarthritis. J Clin Rheumatol. 1999;5:S2-S11.
White et al., Bringing comfort to the masses: a novel evaluation of comfort agent solution properties. Cont Lens Anterior Eye. Apr. 2014;37(2):81-91.
Williams et al., A Crosslinked HA-Based Hydrogel Ameliorates Dye Eye Symptoms in Dogs. International Journal of Biomaterials. Jun. 6, 2013;2013:1-8.
Wysenbeek et al., The effect of sodium hyaluronate on the corneal epithelium. An ultrastructural study. Invest Ophthalmol Vis Sci. Feb. 1988;29(2):194-9.
Ye et al., High molecular weight hyaluronan decreases oxidative DNA damage induced by EDTA in human corneal epithelial cells. Eye (Lond). Jul. 2012;26(7):1012-20.
Yokoi et al., Effectiveness of hyaluronan on corneal epithelial barrier function in dry eye. Br J Ophthalmol. Jul. 1997;81(7):533-6.
Zhao et al., Synthesis and characterization of a novel hyaluronic acid hydrogel. J Biomater Sci Polym Ed. 2006;17(4):419-33.
Zheng et al., Comparison of in vivo efficacy of different ocular lubricants in dry eye animal models. Invest Ophthalmol Vis Sci. Apr. 29, 2014;55(6):3454-60.
International Search Report for Application No. PCT/US2014/045973, dated Oct. 13, 2014.
International Search Report for Application No. PCT/US2016/052743, dated Feb. 27, 2017.
U.S. Appl. No. 14/327,321, filed Jul. 9, 2014, U.S. Pat. No. 9,492,474, Issued.
U.S. Appl. No. 15/290,107, filed Oct. 11, 2016, U.S. Pat. No. 10,383,890, Issued.
U.S. Appl. No. 16/460,511, filed Jul. 2, 2019, U.S. Pat. No. 10,933,085, Issued.
U.S. Appl. No. 17/158,481, filed Jan. 26, 2021, U.S. Publication No. 2021-0161947, Allowed.
U.S. Appl. No. 15/271,434, filed Sep. 21, 2016, U.S. Pat. No. 10,383,889, Issued.
U.S. Appl. No. 16/460,557, filed Jul. 2, 2019, U.S. Pat. No. 10,888,580, Issued.

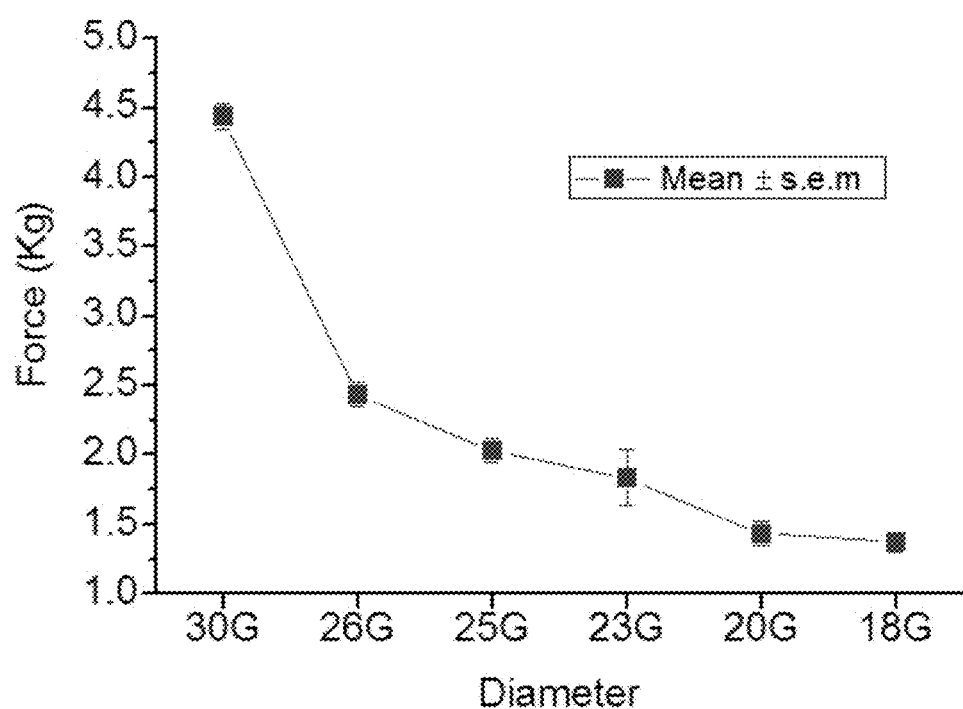

HIGH ELASTICITY HYALURONAN COMPOSITIONS AND METHODS OF USE THEREOF

RELATED APPLICATIONS

This application is a continuation of U.S. application Ser. No. 16/460,557, filed on Jul. 2, 2019; which is a continuation of U.S. application Ser. No. 15/271,434, filed on Sep. 21, 2016, now U.S. Pat. No. 10,383,889, issued on Aug. 20, 2019; which claims the benefit of U.S. Provisional Application Ser. No. 62/232,364, filed on Sep. 24, 2015. The entire contents of each of the foregoing applications are hereby incorporated herein by reference.

BACKGROUND OF THE INVENTION

Hyaluronan or hyaluronic acid (HA) is a high average molecular weight linear polysaccharide which is distributed widely throughout connective, epithelial, and neural tissues. HA is found primarily in the extracellular matrix and pericellular matrix, but has also been shown to occur intracellularly. The biological functions of HA include maintenance of the elastoviscosity of liquid connective tissues such as synovial fluid in the joints and the vitreous of the eye, control of tissue hydration and water transport, supramolecular assembly of proteoglycans in the extracellular matrix, and numerous receptor-mediated roles in cell detachment, mitosis, migration and tumor development.

Some of the known uses of HA include treatment of dry eye conditions, in skin care as dermal fillers and to promote wound healing. Often, dry eye conditions, skin care/dermatological procedures and wound healing are associated with pain and discomfort that typically require a separate administration of an analgesic medication. The HA formulations currently used to treat the above conditions are not effective in treating topical pain. Accordingly, there is a need in the art for methods to treat dry eye conditions effectively, to minimize skin imperfections with injectable augmentation devices, and to promote wound healing while alleviating the pain associated with these conditions.

SUMMARY OF THE INVENTION

The present inventors have discovered that compositions comprising high concentrations of HA, e.g., compositions having HA concentrations of about 30 mg/mL (about 3% weight/volume) or greater can be used effectively to alleviate pain and discomfort associated with dry eye conditions, dermatological procedures, and healing wounds. Without wishing to be bound by a specific theory, it is believed that the effectiveness of the HA compositions of the invention comprising high concentrations of HA for treating pain and discomfort is determined by their high elasticity, as is evidenced by the high value of the elastic modulus G'. It is also believed, without wishing to be bound by a specific theory, that the effectiveness of the HA compositions of the invention is determined by a relatively high probability of interaction of HA molecules with pain transducing channels, such as TRPV1, thereby reducing nociceptor excitability.

Accordingly, the present invention provides a method for alleviating pain and discomfort associated with a dry eye condition in a subject in need thereof. The method comprises administering to an eye of the subject a composition, e.g., a pharmaceutical composition, comprising hyaluronan, wherein: the hyaluronan is present in the composition at a concentration of greater than about 30 mg/mL, e.g., about 35 mg/mL or more, about 40 mg/mL or more, about 45 mg/mL or more, about 50 mg/mL or more, about 55 mg/mL or more, about 60 mg/mL or more, about 65 mg/mL or more, about 70 mg/mL or more, about 75 mg/mL or more, about 80 mg/mL or more, about 85 mg/mL or more, about 90 mg/mL or more, about 95 mg/mL or more or about 100 mg/mL or more; the hyaluronan has an average molecular weight of between about 1 and about 2 million; and the hyaluronan is not cross-linked and/or is substantially free of chemical modifications, thereby alleviating the pain and discomfort in the subject.

In another aspect, the hyaluronan is present in the composition at a concentration of about 40 mg/mL to about 60 mg/mL.

In some embodiment, the present invention also provides a method for alleviating pain and discomfort associated with a dry eye condition in a subject in need thereof, which comprises administering to an eye of the subject a composition, e.g., a pharmaceutical composition, comprising hyaluronan, wherein: the hyaluronan is present in the composition at a concentration of at least about 40 mg/mL; the hyaluronan has an average molecular weight of between about 1 and about 2 million; and the hyaluronan is not cross-linked and/or is substantially free of chemical modifications, thereby alleviating the pain and discomfort in the subject.

In some embodiments, the composition is substantially free of other pharmaceutically active substances.

In certain aspects, the composition does not comprise a polyglycol.

In some embodiments, the composition further comprises a buffer, e.g., phosphate buffered saline (PBS).

In some embodiments, the composition has an elasticity of at least about 200 Pascal when measured at a frequency of 0.5 Hz; at least about 1,000 Pascal when measured at a frequency of 0.5 Hz; at least about 2,000 Pascal when measured at a frequency of 0.5 Hz; or at least about 4,000 Pascal when measured at a frequency of 0.5 Hz.

In some embodiments, the composition is in the form of a gel, an ointment, a liniment, a lotion or a cream.

In some aspects, the composition is administered to the ocular surface, such as under the eye lid, e.g., under the upper or lower eye lid, of the subject or at the cornea-eyelid interface.

In certain embodiments, the composition is administered to the subject immediately prior to rest or sleep.

In some aspects, the composition is administered without an injection into the eye of the subject.

In some aspects, the composition is administered using a container, e.g., a single dose container, such as a soft plastic bottle, a tube, an airless tube, an eye cup, a dropper or a cartridge.

In some embodiments, the dry eye condition is associated with one or more symptoms selected from the group consisting of ocular dryness; decreased tear production, volume, and flow; abnormal tear composition; increased tear osmolarity; keratitis; conjunctival and corneal staining; redness; blurry vision; decreased tear film break-up time; increased conjunctival redness; excess debris in tear film, ocular grittiness; ocular burning; foreign body sensation in the eye; excess tearing; photophobia; ocular stinging; refractive impairment; ocular sensitivity; and ocular irritation. In other embodiments, the dry eye condition is associated with a condition selected from the group consisting of an autoimmune disorder; an ocular surgery; ingestion of a medication; dry environmental conditions; prolonged computer use; ocular fatigue; prolonged contact lens wear, corneal sensitivity;

partial lid closure; surface irregularities; eye lid irregularities; and a condition associated with corneal nociceptive pain associated with corneal injury or a condition associated with neuropathic pain. In one further embodiment, the dry eye condition is associated with an ocular surgery, and the ocular surgery is selected from the group consisting of photorefractive surgery, such as photorefractive keratectomy (PRK), cataract surgery, retinal detachment surgery, laser-assisted in situ keratomileusis (LASIK), and any corneal surgical procedure involving damage to corneal sensory nerves. In a further embodiment, the dry eye condition is associated with a condition associated with neuropathic pain, e.g., a cataract or a retinal detachment, or surgery designed to treat cataract or retinal detachment.

In some aspects, the composition is administered daily for 3 days, 4 days, 5 days, 6 days, 1 week, 2 weeks, 4 weeks or 10 weeks. In other aspects, long term amelioration, e.g., 8 hours, 12 hours, 24 hours, 1 day, 3 days, 5 days, 7 days, 14 days or 28 days, of the pain and discomfort is achieved in the subject.

In some embodiments, the subject is a mammal, e.g., a human.

In yet another aspect, the present invention also provides a method for alleviating pain and discomfort while minimizing at least one skin imperfection in a subject in need thereof. The method comprises administering to the subject a composition comprising hyaluronan, wherein: the hyaluronan is present in the composition at a concentration of greater than about 30 mg/mL; the hyaluronan has an average molecular weight of between about 1 and about 2 million; the hyaluronan is not cross-linked and/or is substantially free of chemical modifications; and wherein the composition is substantially free of other pharmaceutically active substances, thereby alleviating the pain and minimizing the at least one skin imperfection.

In some embodiments, the hyaluronan is present at a concentration of about 40 mg/mL to about 60 mg/mL.

In a further aspect, the present invention also provides a method for alleviating pain and discomfort while minimizing at least one skin imperfection in a subject in need thereof, which comprises administering to the subject a composition comprising hyaluronan, wherein: the hyaluronan is present in the composition at a concentration of at least about 40 mg/mL; the hyaluronan has an average molecular weight of between about 1 and about 2 million; the hyaluronan is not cross-linked and/or is substantially free of chemical modifications; and wherein the composition is substantially free of other pharmaceutically active substances, thereby alleviating the pain and minimizing the at least one skin imperfection.

In some embodiments, the other pharmaceutically active substance is a local anesthetic, e.g., lidocaine or bupivacaine.

In certain aspects, the composition also comprises a buffer, e.g., phosphate buffered saline (PBS).

In some embodiments, the composition has an elasticity of at least about 200 Pascal when measured at a frequency of 0.5 Hz; at least about 1,000 Pascal when measured at a frequency of 0.5 Hz; at least about 2,000 Pascal when measured at a frequency of 0.5 Hz; or at least about 4,000 Pascal when measured at a frequency of 0.5 Hz.

In some aspects, the composition is sterile.

In certain embodiments, the composition is administered by an injection into the skin of the subject. In a further embodiment, the composition is injected into the face of the subject. For example, the composition is injected into a region selected from the group consisting of nasolabial region, upper lip region, forehead, eye region and cheek region.

In some aspects, the composition is administered by an injection using a pre-filled syringe, e.g., a 1, 2, 3, 4, 5, 6, 7, 8, 9 or 10-mL pre-filled syringe. In a further aspect, the pre-filled syringe is sterilized.

In another aspect, the present invention also provides a method for alleviating pain and discomfort while facilitating wound healing in a subject in need thereof. The method comprises administering to the subject a composition, e.g., a pharmaceutical composition, comprising hyaluronan, wherein: the hyaluronan is present in the composition at a concentration of greater than about 30 mg/mL; the hyaluronan has an average molecular weight of between about 1 and about 2 million; and the hyaluronan is not cross-linked and/or is substantially free of chemical modifications, thereby alleviating the pain and facilitating the wound healing.

In one further embodiment, the hyaluronan is present at a concentration of about 40 mg/mL to about 60 mg/mL.

In a further aspect, the present invention also provides a method for alleviating pain and discomfort while facilitating wound healing in a subject in need thereof, which comprises administering to the subject a composition, e.g., a pharmaceutical composition, comprising hyaluronan, wherein: the hyaluronan is present in the composition at a concentration of at least about 40 mg/mL; the hyaluronan has an average molecular weight of between about 1 and about 2 million; and the hyaluronan is not cross-linked and/or is substantially free of chemical modifications, thereby alleviating the pain and facilitating the wound healing.

In some aspects, the composition is substantially free of other pharmaceutically active substances, such as local anesthetics, e.g., lidocaine or bupivacaine.

In some embodiments, the composition further comprises a buffer, e.g., phosphate buffered saline (PBS).

In some aspects, the composition has an elasticity of at least about 200 Pascal when measured at a frequency of 0.5 Hz; at least about 1,000 Pascal when measured at a frequency of 0.5 Hz; at least about 2,000 Pascal when measured at a frequency of 0.5 Hz; or at least about 4,000 Pascal when measured at a frequency of 0.5 Hz.

In some embodiments, the composition is sterile.

In certain embodiments, the composition is administered topically, e.g., on the surface of a wound or a scar on the skin.

BRIEF DESCRIPTION OF THE DRAWINGS

FIG. 1 is a graph depicting the pressure required to eject a 4% HA solution through needles of different sizes.

DETAILED DESCRIPTION OF THE INVENTION

The present invention provides methods for alleviating pain and discomfort associated with a dry eye condition; skin care/dermatological treatments and wound healing. The presently claimed methods comprise administering HA compositions comprising high concentrations of hyaluronan (HA), e.g., greater than about 30 mg/mL or more. Such compositions were determined to have high elasticity, e.g., high elastic modulus G', when measured at frequencies of 0.1-10 Hz. HA compositions characterized by high elasticity, e.g., compositions comprising high concentrations of HA, are surprisingly effective at alleviating pain and discomfort resulting from a dry eye condition; a cosmetic treatment; or wound healing. Without wishing to be bound by a specific theory, it is believed that the effectiveness of the HA compositions of the invention comprising high concentrations of HA at treating pain and discomfort is determined by their high elasticity, as is evidenced by the high value of the elastic modulus G'. It is also believed, without wishing to be bound by a specific theory, that the effectiveness of the HA compositions of the invention is determined by a relatively high probability of interaction of HA molecules with pain transducing channels, such as TRPV1, thereby reducing nociceptor excitability. The average molecular weight of HA used in the methods of the invention may be 2 million or less, e.g., between about 1-2 million.

I. Hyaluronan Compositions for Use in the Methods of the Invention

The present invention provides methods that comprise administering to a subject in need thereof compositions comprising hyaluronan (HA). In some embodiments, the composition comprises hyaluronan, wherein the hyaluronan is present in the composition at a concentration of greater than about 30 mg/mL (or greater than about 3% weight/volume); the hyaluronan has an average molecular weight of between about 1 and about 2 million; and the hyaluronan is not cross-linked and/or is substantially free of chemical modifications.

For example, the hyaluronan concentration in the composition may be about 30 mg/mL (or about 3% w/v), about 35 mg/mL (or about 3.5% w/v), about 40 mg/mL (or about 4% w/v), about 45 mg/mL (or about 4.5% w/v), about 50 mg/mL (or about 5% w/v), about 55 mg/mL (or about 5.5% w/v), about 60 mg/mL (or about 6% w/v), about 65 mg/mL (or about 6.5% w/v), about 70 mg/mL (or about 7% w/v), about 75 mg/mL (or about 7.5% w/v), about 80 mg/mL (or about 8% w/v), about 85 mg/mL (or about 8.5% w/v), about 90 mg/mL (or about 9% w/v), about 95 mg/mL (or about 9.5% w/v), about 100 mg/mL (or about 10% w/v), about 105 mg/mL (or about 10.5% w/v), about 110 mg/mL (or about 11% w/v) about 115 mg/mL (or about 11.5% w/v), about 120 mg/mL (or about 12% w/v), about 125 mg/mL (or about 12.5% w/v), about 130 mg/mL (or about 13% w/v), about 135 mg/mL (or about 13.5% w/v), about 140 mg/mL (or about 14% w/v), about 145 mg/mL (or about 14.5% w/v), or about 150 mg/mL (or about 15% w/v). In a specific embodiment, the HA is present in the composition at a concentration of about 40 mg/mL (or about 4% w/v). In other specific embodiments, the HA is present in the composition of the invention at the concentration of about 41 mg/mL (or about 4.1% w/v), about 42 mg/mL (or about 4.2% w/v), about 43 mg/mL (or about 4.3% w/v), about 44 mg/mL (or about 4.4% w/v), about 45 mg/mL (or about 4.5% w/v), about 46 mg/mL (or about 4.6% w/v), about 47 mg/mL (or about 4.7% w/v), about 48 mg/mL (or about 4.8% w/v), about 49 mg/mL (or about 4.9% w/v), about 50 mg/mL (or about 5.0% w/v), about 51 mg/mL (or about 5.1% w/v), about 52 mg/mL (or about 5.2% w/v), about 53 mg/mL (or about 5.3% w/v), about 54 mg/mL (or about 5.4% w/v), about 55 mg/mL (or about 5.5% w/v), about 56 mg/mL (or about 5.6% w/v), about 57 mg/mL (or about 5.7% w/v), about 58 mg/mL (or about 5.8% w/v), 59 mg/mL (or about 5.9% w/v) or about 60 mg/mL (or about 6% w/v).

In some examples, the hyaluronan concentration in the composition may be greater than about 30 mg/mL (or about 3% w/v), e.g., greater than about 31 mg/mL (or about 3.1%), greater than about 32 mg/mL (or about 3.2%), greater than about 33 mg/mL (or about 3.3%), greater than about 34 mg/mL (or about 3.4%), greater than about 35 mg/mL (or about 3.5%), greater than about 36 mg/mL (or about 3.6%), greater than about 37 mg/mL (or about 3.7%), greater than about 38 mg/mL (or about 3.8%), or greater than about 39 mg/mL (or about 3.9%).

In some examples, the hyaluronan concentration in the composition may have an average molecular weight of between about 1 and about 2 million; e.g., between about 1.1 and about 2 million, between about 1.2 and about 2 million, between about 1.3 and about 2 million, between about 1.4 and about 2 million, between about 1.5 and about 2 million or between about 1.6 and about 2 million.

In certain embodiments, the hyaluronan used in the compositions is not cross-linked and/or is free of chemical modifications. For example, the hyaluronan used in the compositions is free from amidation that may be formed by a reaction between the carboxyl group of HA and the amine group of a derivatizing agent as described, e.g., in EP Patent No. 1095064 B1. The hyaluronan used in the compositions may also be free from chemical modifications and/or cross-links that may result from the reaction of hyaluronan with a carbodiimide, such as a monocarbodiimide or a biscarbodiimide, as described, for example, in U.S. Pat. No. 8,323,617. In some cases, the hyaluronan used in the compositions may also be free from acrylates, e.g., methacrylates as described in U.S. Publication No. 2010/0048755; sulfates as described, e.g., in U.S. Publication No. 2013/0209531; and deuterium, as described, e.g., in U.S. Publication No. 2015/0148310.

In some embodiments, the HA compositions of the invention are free from other pharmaceutically active substances. As used herein, a "pharmaceutically active substance" is a substance that is capable of exerting a biological effect on a subject, e.g., a human or an animal subject. The term "pharmaceutically active substance" also comprises substances that can modulate the biological effect of an HA composition when the composition is administered to a subject, e.g., alleviate pain and discomfort associated with a dry eye condition; a skin care/dermatological treatment, or a healing wound. In certain embodiments, the pharmaceutically active substance is a protein, e.g., a bone morphogenic protein (BMP), such as rhGDF-5. In certain embodiments, the pharmaceutically active substance is a glycosaminoglycan (GAG) that is different from HA, e.g., chondroitin. In some embodiments, the pharmaceutically active substance is hydroxypropyl methyl cellulose. In other embodiments, the pharmaceutically active substance is a topical anesthetic, such as a lidocaine or a bupivacaine. In some cases, the pharmaceutically active substance is a purinergic receptor agonist, e.g., a $P2Y_2$ receptor agonist.

In certain embodiments, the HA compositions of the invention are free from molecules capable of scavenging free radicals, such as a polyol, e.g., sorbitol, maltitol, xylitol or isomalt. In other embodiments, the HA compositions used in the methods of the invention are free from molecules that diminish the elasticity of HA, for example, dextran or sucrose.

In some cases, the HA compositions used in the methods of the invention are free from a polyglycol, e.g., polyethylene glycol.

An HA composition may consist essentially of HA present at a concentration of greater than about 30 mg/mL (about 3% w/v), or about 40 mg/mL (about 4% w/v) in a physiological buffer, e.g., a phosphate buffer or a bicarbonate buffer, and having the average molecular weight of between about 1 million and about 2 million. For example, an HA composition used in the methods of the invention consists essentially of HA present at a concentration of about 40 mg/mL (or about 4% w/v), and having the average molecular weight of between about 1 million and about 2 million.

The hyaluronan in the compositions used in the methods of the invention may have an elasticity of at least 100 Pascal when measured at a frequency of 0.5 Hz, or an elasticity of at least 400 Pascal when measured at a frequency of 0.5 Hz, or an elasticity of at least 1,000 Pascal when measured at a frequency of 0.5 Hz, or an elasticity of at least 2,000 Pascal when measured at a frequency of 0.5 Hz, or an elasticity of at least 4,000 Pascal when measured at a frequency of 0.5 Hz, or an elasticity of between 400 and 5,000 Pascal when measured at a frequency of 0.5 Hz.

It should be appreciated that a variety of methods are available for measuring the elasticity of a biopolymer such as hyaluronan. In one embodiment, the elasticity of compositions comprising hyaluronan is measured as pressure (expressed in Pascal) at a specific frequency (expressed in Hertz). For instance, the frequencies that may be used to evaluate the elasticity of the hyaluronan compositions provided herein, may be measured at 0.5 Hz, 2.5 Hz, or 5.0 Hz.

It should further be appreciated that the elasticity may be expressed in any relevant frequency. Thus, for instance, in one embodiment, the elasticity is expressed based on a frequency of 2.5 Hz and a composition comprising hyaluronan with high elasticity is a composition with an elasticity of at least 200 Pa at a frequency of 2.5 Hz. Similarly, in one embodiment, the elasticity is expressed based on a frequency of 5.0 Hz and a composition comprising hyaluronan with high elasticity is a composition having an elasticity of at least 400 Pa at a frequency of 5.0 Hz.

In one embodiment, a composition comprising hyaluronan for use in the presently claimed methods has an elasticity of at least 100 Pascal when measured at a frequency of 0.5 Hz. In some embodiments, the composition has an elasticity of at least 300 Pascal when measured at a frequency of 2.5 Hz. In some embodiments, the composition has an elasticity of at least 350 Pascal when measured at a frequency of 5.0 Hz.

In a further embodiment, a composition comprising hyaluronan has an elasticity of at least 400 Pascal when measured at a frequency of 0.5 Hz. In some embodiments, the composition has an elasticity of at least 750 Pascal when measured at a frequency of 2.5 Hz. In some embodiments, the composition has an elasticity of at least 900 Pascal when measured at a frequency of 5.0 Hz.

In another embodiment, a composition comprising hyaluronan has an elasticity of at least 1000 Pascal when measured at a frequency of 0.5 Hz. In some embodiments, the composition has an elasticity of at least 1600 Pascal when measured at a frequency of 2.5 Hz. In some embodiments, the composition has an elasticity of at least 2000 Pascal when measured at a frequency of 5.0 Hz.

In yet another embodiment, a composition comprising hyaluronan has an elasticity of at least 2600 Pascal when measured at a frequency of 0.5 Hz. In some embodiments, the composition has an elasticity of at least 4000 Pascal when measured at a frequency of 2.5 Hz. In some embodiments, the composition has an elasticity of at least 4500 Pascal when measured at a frequency of 5.0 Hz.

In one embodiment, a composition comprising hyaluronan has an elasticity of at least 4000 Pascal when measured at a frequency of 0.5 Hz. In some embodiments, the composition has an elasticity of at least 5000 Pascal when measured at a frequency of 2.5 Hz. In some embodiments, the composition has an elasticity of at least 6000 Pascal when measured at a frequency of 5.0 Hz.

In some embodiments, the composition has an elasticity of between 100 and 10,000 Pascal when measured at a frequency of 0.5 Hz. In some embodiments, the composition has an elasticity of between 400 and 5,000 Pascal when measured at a frequency of 0.5 Hz. In some embodiments, the composition has an elasticity of between 1,000 and 2,000 Pascal when measured at a frequency of 0.5 Hz.

In some embodiments, the composition has an elasticity of between 300 and 10,000 Pascal when measured at a frequency of 2.5 Hz. In some embodiments, the composition has an elasticity of between 750 and 6,000 Pascal when measured at a frequency of 2.5 Hz. In some embodiments, the composition has an elasticity of between 1,500 and 4,000 Pascal when measured at a frequency of 2.5 Hz.

In some embodiments, the composition has an elasticity of between 300 and 10,000 Pascal when measured at a frequency of 5.0 Hz. In some embodiments, the composition has an elasticity of between 900 and 7,000 Pascal when measured at a frequency of 5.0 Hz. In some embodiments, the composition has an elasticity of between 2,000 and 5,000 Pascal when measured at a frequency of 5.0 Hz.

In some embodiments, the elasticity may be measured by using a suitable device (e.g., a rheometer). For example, the elasticity may be measured by using a Stresstech High Resolution Research Rheometer (Reologica Instruments AB). Typically, the elasticity is determined at ambient temperature and pressure; however, it should be appreciated that elasticity may also be measured at non-ambient temperature and/or pressure. It should further be appreciated that a person of ordinary skill in the art knows how to convert a magnitude of elasticity determined at various temperatures and pressures into a magnitude of elasticity at ambient temperature and pressure.

High elasticity compositions of hyaluronan can be prepared by increasing the concentration of hyaluronan in the composition. Thus, in one aspect, the presently claimed methods utilize compositions having high elasticity that comprise a high percentage of hyaluronan. For example, the compositions may comprise at least 3.0% of hyaluronan (weight by volume), at least 3.5% of hyaluronan (weight by volume), at least 4.0% of hyaluronan (weight by volume), at least 4.5% of hyaluronan (weight by volume), at least 5.0% of hyaluronan (weight by volume), at least 5.5% of hyaluronan (weight by volume), at least 6.0% of hyaluronan (weight by volume), at least 6.5% of hyaluronan (weight by volume), at least 7.0% of hyaluronan (weight by volume), at least 7.5% of hyaluronan (weight by volume), at least 8.0% of hyaluronan (weight by volume), at least 8.5% of hyaluronan (weight by volume), at least 8.9% of hyaluronan (weight by volume), at least 9.0% of hyaluronan (weight by volume), at least 10.0% of hyaluronan (weight by volume), at least 11.0% of hyaluronan (weight by volume), at least 12.0% of hyaluronan (weight by volume), at least 13.0% of hyaluronan (weight by volume), at least 14.0% of hyaluronan (weight by volume), or at least 15.0%, or more, of hyaluronan (weight by volume).

Ranges intermediate to the recited values are also intended to be included in the compositions for use in the methods of this invention. For example, hyaluronan content in the compositions may be between about 3% and about 15% (weight/volume), between about 3% and about 10% (weight/volume), about 3.5% and about 9% (weight/volume), about 4% and about 8% (weight/volume), or about 5% and about 7% (weight/volume).

It should further be appreciated that the amount of hyaluronan in a particular volume may also be expressed by alternative means (e.g., gram/liter or mol/liter). A person of ordinary skill in the art would know how to convert the various means of expressing the amount of hyaluronan in a particular volume.

Compositions of hyaluronan with a high concentration of hyaluronan, even with an average molecular weight of about 1-2 million, are particularly effective in the treatment of pain, e.g., pain associated with a dry eye condition, a cosmetic treatment or a healing wound. Thus, the hyaluronan comprised in the HA compositions described herein may have an the average molecular weight that falls within the range of between 1 and 2 million and is also less than 2 million, less than 1.9 million, less than 1.8 million, less than 1.7 million, less than 1.6 million, less than 1.5 million, less than 1.4 million, less than 1.3 million, less than 1.2 million, less than 1.1 million, less than 1 million, less than 0.9 million, less than 0.8 million, less than 0.7 million, less than 0.6 million, or less than 0.5 million. In other cases, the hyaluronan comprised in the HA compositions described herein may have an the average molecular weight that falls within the range of between 1 and 2 million and is also greater than 0.1 million, greater than 0.2 million, greater than 0.3 million, greater than 0.4 million, greater than 0.5 million, greater than 0.6 million, greater than 0.7 million, greater than 0.8 million, greater than 0.9 million, greater than 1 million, greater than 1.1 million, greater than 1.2 million, greater than 1.3 million, greater than 1.4 million, greater than 1.5 million, greater than 1.6 million, greater than 1.7 million, greater than 1.8 million or greater than 1.9 million.

Ranges intermediate to the recited values are also intended to be part of this invention. For example, in the compositions of hyaluronan provided herein, the average molecular weight of hyaluronan is between 1 and 2 million, between 1 and 1.5 million, between 0.5 and 1 million, between 0.5 and 2 million, or between 0.9 and 1.4 million.

In some embodiments of the compositions of hyaluronan described herein, the majority of the hyaluronan present in the composition falls within the average molecular weight range described herein. Thus, for instance, in compositions with an average molecular weight of hyaluronan of between 0.2 and 2 million, at least 95% of the hyaluronan present in the composition falls within the range of between 0.2 and 2 million. In some embodiments, at least 50% of the hyaluronan present in the compositions provided herein falls within the recited range of average molecular weight. In some embodiments, at least 60% of the hyaluronan present in the compositions provided herein falls within the recited range of average molecular weight. In some embodiments, at least 70% of the hyaluronan present in the compositions provided herein falls within the recited range of average molecular weight. In some embodiments, at least 80% of the hyaluronan present in the compositions provided herein falls within the recited range of average molecular weight. In some embodiments, at least 90% of the hyaluronan present in the compositions provided herein falls within the recited range of average molecular weight. In some embodiments, at least 95% of the hyaluronan present in the compositions provided herein falls within the recited range of average molecular weight. In some embodiments, at least 98% of the hyaluronan present in the compositions provided herein falls within the recited range of average molecular weight. In some embodiments, at least 99% of the hyaluronan present in the compositions provided herein falls within the recited range of average molecular weight. In some embodiments, at least 99.9% of the hyaluronan present in the compositions provided herein falls within the recited range of average molecular weight.

II. Sources of Hyaluronan

The hyaluronan used in the compositions and methods described herein may be obtained from any source. In general, hyaluronan has the same chemical structure, regardless of its origin (e.g., chicken or rooster comb, human tissue or bacterial cell wall). Hyaluronan can be obtained, for instance, from chicken or rooster comb, from bacterial cell walls and from human tissue (umbilical cord, vitreous of the eye, synovial fluid from the joints, etc.). In some embodiments, the hyaluronan is isolated from chicken combs. In some embodiments, the hyaluronan is isolated from human tissue e.g., umbilical cord, vitreous of the eye, synovial fluid from the joints. In some embodiments, the hyaluronan is isolated from cell culture. In some embodiments, the hyaluronan is isolated from bacterial cell walls. The isolation of hyaluronan from various sources is known to a person of ordinary skill in the art. For instance, the harvest and purification of hyaluronan from rooster combs is described in U.S. Pat. No. 4,141,973, while the harvest and purification of hyaluronan from bacterial sources is described in U.S. Pat. No. 4,517,295. In some embodiments, the hyaluronan is purified and harvested to a solution with 0.15 M NaCl at a pH of 6-8. Generally, the hyaluronan obtained from the various sources will be free of proteins or glycosaminoglycans other than hyaluronan.

In some embodiments, the isolated hyaluronan is further purified to obtain hyaluronan with a desired average molecular weight range (e.g., through column chromatography). Methods for purifying hyaluronan with a desired average molecular weight range are known to a person of ordinary skill in the art.

In one aspect, the hyaluronan with high elasticity disclosed herein is unmodified hyaluronan. However, it should be appreciated that in some embodiments, the hyaluronan may be chemically modified. For instance, the hyaluronan may be chemically modified to increase the elasticity of the hyaluronan.

III. Sterilization of the Hyaluronan Compositions

In some embodiments, the HA compositions described herein and used in the methods of the invention are sterile. A "sterile composition", as used herein, refers to a composition that is safe to be administered to a subject, e.g., a human subject. Thus, a sterile composition will only have a minimal number of agents that can cause unwanted side effects such as an unwanted tissue response, immune response, an inflammation or an infection.

Methods for sterilizing compositions of hyaluronan are known in the art and include, for example, heat or steam sterilization, e.g., by autoclaving. In some embodiments, the HA compositions of the invention are sterilized by heating the compositions. In some embodiments, the HA compositions of the invention are sterilized by including the HA composition in a syringe and autoclaving the HA containing syringe at 131° C. for 2 minutes or 121° C. for 15 minutes followed by immediate cooling.

IV. Additional Components for the Hyaluronan Compositions

The HA compositions described herein may include additional components that may stabilize the hyaluronan and/or make the composition more suitable for administration to a subject. In some embodiments, the HA compositions of the invention may include a buffer. Buffers are added in order to allow for a stable pH. Suitable buffers for use in the present invention include phosphate buffers and bicarbonate buffers. In some embodiments, the buffer is a tris-phosphate buffer. In some embodiments, the buffer is present in a concentration of between 1 mM and 100 mM, between 2 mM and 50 mM, or between 5 mM and 20 mM. In some embodiments, the buffer concentration is less than 1 mM. In some embodiments, the buffer concentration is more than 100 mM. In some embodiments, the buffer concentration is 10 mM. It should be appreciated that the buffer concentration is dependent on the nature of the buffer that is being used. In some embodiments, the pH of the composition is between pH 7 and pH 9 or between pH 7.5 and pH 8.5. In some embodiments, the pH of the composition is 8.0. In some embodiments, the pH of the composition is 7.5. In some embodiments, the pH of the composition is 8.5. If needed, acid (such as HCL) or base (such as NaOH) can be added to the composition to attain the desired pH.

For example, the HA compositions may include a buffer, e.g., a physiologically compatible buffer, but do not include any additional components.

The HA compositions may also include a stabilizing excipient, such as carboxylic acid or a salt thereof. In some embodiments, the composition includes a monocarboxylic acid and/or salt thereof. In some embodiments, the composition includes a gluconic acid and/or sodium gluconate. In some embodiments, the composition includes a dicarboxylic acid and/or a salt thereof. In some embodiments, the composition includes a citric acid, succinic acid, malonic acid, maleic acid, tartaric acid and or a salt thereof. In some embodiments, the carboxylic acid is sodium citrate. In some embodiments, the composition includes a tricarboxylic aid (TCA) and/or a salt thereof. In some embodiments, the composition includes a nitrilotriacetic acid and/or sodium nitrilotriacetic acid. In some embodiments, the composition includes a tetracarboxylic acid and/or salt thereof. In some embodiments, the composition includes an ethylenediaminetetracetic acid (EDTA) and/or sodium EDTA. In some embodiments, the composition includes a pentacarboxylic acid and/or a salt thereof. In some embodiments, the composition includes a diethylenetriaminepentaacetic acid (DTPA) and/or sodium DTPA. Suitable carboxylic acids include, but are not limited to, citrate compounds, such as sodium citrate; tartrate compounds, succinate compounds, and EDTA. Kaushil et al. in Protein Science 1999 8: 222-233, and Busby et al. in the Journal of Biological Chemistry Volume 256, Number 23 pp 12140-1210-12147 describe carboxylic acids and their uses. In some embodiments, the stabilizing excipient has a concentration of between 50 to 600 mM, between 250 to 500 mM, or between 250 to 350 mM. In some embodiments, the concentration of the stabilizing excipient is 300 mM. In some embodiments, the concentration of the stabilizing excipient is less than 100 mM. In some embodiments, the concentration of the stabilizing excipient is more than 600 mM.

The HA compositions described herein may also include a sugar (e.g., a disaccharide sugar). Disaccharide sugars that can be added to the composition include, but are not limited to, sucrose, lactulose, lactose, maltose, trehalose, cellobiose, dextrose and dextran. In some cases, the sugar may be present at between 0.5 to 5% (wt/volume). In some cases, the sugar may be present at between 1 to 2% (wt/volume). In one embodiment, the sugar may be present at 1%. In some embodiments, the sugar may be present at less than 1% (wt/volume). In some embodiments, the sugar may be present at more than 5% (wt/volume). In one embodiment, the sugar may be sucrose or trehalose and is present at 1% (wt/volume).

In some embodiments, the HA compositions described herein may include salts. Salts that can be used in the compositions include sodium chloride and other physiological compatible salts. In some embodiments, the salt concentration present in the HA compositions described herein is between about 10 mM and about 250 mM, between about 25 mM and about 100 mM, between about 30 mM and about 70 mM, between about 45 mM and about 150 mM, between about 125 mM and about 200 mM, between about 150 mM and about 250 mM, or between about 190 mM and about 250 mM. In some embodiments, the salt concentration is 50 mM. In some embodiments, the salt concentration is less than 10 mM. In some embodiments, the salt concentration is more than 250 mM. In a specific embodiment, the salt concentration is between about 50 mM and about 200 mM.

In some embodiments, the HA compositions of the invention may have a normal osmolarity, e.g., about 310 mOsm/L. In other embodiments, the HA compositions of the invention may have an osmolarity that is below the normal osmolarity, e.g., below 310 mOsm/L. For example, the HA compositions of the invention may have osmolarity of between about 20 mOsm/L and about 500 mOsm/L, e.g., between about 150 and about 310 mOsm/L, between about 150 and about 200 mOsm/L, between about 160 and about 220 mOsm/L, between about 180 and about 250 mOsm/L, between about 200 and about 300 mOsm/L, between about 250 and about 310 mOsm/L, between about 290 and about 310 mOsm/L, between about 250 and about 290 mOsm/L or between about 270 and about 300 mOsm/L. In some embodiments, the osmolarity of the HA compositions of the invention may be about 150 mOsm/L, about 155 mOsm/L, about 160 mOsm/L, about 165 mOsm/L, about 170 mOsm/L, about 175 mOsm/L, about 180 mOsm/L, about 185 mOsm/L, about 190 mOsm/L, about 195 mOsm/L, about 200 mOsm/L, about 205 mOsm/L, about 210 mOsm/L, about 215 mOsm/L, about 220 mOsm/L, about 225 mOsm/L, about 230 mOsm/L, about 235 mOsm/L, about 240 mOsm/L, about 245 mOsm/L, about 250 mOsm/L, about 255 mOsm/L, about 260 mOsm/L, about 265 mOsm/L, about 270 mOsm/L, about 275 mOsm/L, about 280 mOsm/L, about 285 mOsm/L, about 290 mOsm/L, about 295 mOsm/L, about 300 mOsm/L, about 305 mOsm/L or about 310 mOsm/L. In one specific embodiment, the osmolarity of the HA compositions of the invention is between about 100 mOsm/L and about 400 mOsm/L, e.g., about 100 mOsm/L, about 110 mOsm/L, about 120 mOsm/L, about 130 mOsm/L, about 140 mOsm/L or about 150 mOsm/L.

In some embodiments, the HA compositions described herein include one or more antioxidants. Antioxidants are substances capable of inhibiting oxidation by removing free radicals from solution. Antioxidants are well known to those of ordinary skill in the art and include materials such as ascorbic acid, ascorbic acid derivatives (e.g., ascorbylpalmitate, ascorbylstearate, sodium ascorbate, or calcium ascorbate), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, d-alpha tocopherol succinate, beta tocopherol, delta tocopherol, gamma tocopherol, and d-alpha tocopherol polyoxyethylene glycol 1000 succinate) monothioglycerol and sodium sulfite. Such materials are typically added in ranges from 0.01 to 2.0%.

In some embodiments, the HA compositions may include one or more isotonicity agents. This term is used in the art interchangeably with iso-osmotic agent, and is known as a compound which can be added to a composition to increase the osmotic pressure, such as an osmotic pressure of 0.9% sodium chloride solution, which is iso-osmotic with human extracellular fluids, such as plasma. Preferred isotonicity agents that can be used in the HA compositions include are sodium chloride, mannitol, sorbitol, lactose, dextrose and glycerol.

In some embodiments, the HA compositions of the invention may include one or more preservatives. Suitable preservatives include but are not limited to: chlorobutanol (0.3-0.9% w/v), parabens (0.01-5.0%), thimerosal (0.004-0.2%), benzyl alcohol (0.5-5%), phenol (0.1-1.0%), and the like.

In some embodiments, the HA compositions may include components that are suitable for ophthalmic use.

In some embodiments, the HA compositions may include one or more components that minimize unwanted side-effects during injection of the composition.

V. Hyaluronan Compositions for Ophthalmic Uses

The present invention provides methods for alleviating pain and discomfort associated with a dry eye condition by administering to an eye of a subject compositions containing HA.

Any of a variety of carriers may be used in the HA compositions for ophthalmic use, including water, mixtures of water and water-miscible solvents, such as C1- to C7-alkanols, vegetable oils or mineral oils comprising from 0.5 to 5% non-toxic water-soluble polymers, natural products, such as gelatin, alginates, pectins, tragacanth, karaya gum, xanthan gum, carrageenin, agar and acacia, starch derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. The concentration of the carrier is, typically, from 1 to 100,000 times the concentration of the active ingredient.

Additional ingredients that may be included in the HA compositions for ophthalmic use include tonicity enhancers, preservatives, solubilizers, non-toxic excipients, demulcents, sequestering agents, pH adjusting agents, co-solvents and viscosity building agents.

For the adjustment of the pH, preferably to a physiological pH, buffers may especially be useful. The pH of the hyaluronan compositions suitable for administration to the eye should be maintained within the range of 4.0 to 8.0, more preferably about 4.0 to 6.0, more preferably about 6.5 to 7.8. Suitable buffers may be added, such as boric acid, sodium borate, potassium citrate, citric acid, sodium bicarbonate, tris(hydroxymethyl)aminomethane (TRIS), and various mixed phosphate buffers (including combinations of $Na_2HPO_4$, $NaH_2PO_4$ and $KH_2PO_4$) and mixtures thereof. Generally, buffers will be used in amounts ranging from about 0.05 to 2.5 percent by weight, and preferably, from 0.1 to 1.5 percent.

Tonicity is adjusted, if needed, typically by tonicity enhancing agents. Such agents may, for example, be of an ionic and/or a non-ionic type. Examples of ionic tonicity enhancers include alkali metal or earth metal halides, such as, for example, $CaCl_2$), KBr, KCl, LiCl, NaI, NaBr or NaCl, $Na_2SO_4$ or boric acid. Non-ionic tonicity enhancing agents include, for example, urea, glycerol, sorbitol, mannitol, propylene glycol, or dextrose. The osmolarity of hyaluronan compositions used in the methods of the present invention may be adjusted with tonicity agents to approximate the osmotic pressure of normal lachrymal fluids which is equivalent to a 0.9% solution of sodium chloride or a 2.5% solution of glycerol. In some examples, an osmolarity of between about 100 mOsm/L and about 150 mOsm/L is preferred, e.g., 100 mOsm/L, 110 mOsm/L, 120 mOsm/L, 120 mOsm/L, 130 mOsm/L, 140 mOsm/L or 150 mOsm/L.

In other examples, an osmolality of between about 225 and 400 mOsm/L is preferred, e.g., between about 280 and about 320 mOsm/L, or between about 297 and about 318 mOsm/L. In some cases, the average osmolarity can fluctuate between about 303.7 and about 306.7 mOsm/L.

In certain embodiments, the HA compositions for ophthalmic use may additionally comprise a preservative. A preservative may, typically, be selected from a quaternary ammonium compound such as benzalkonium chloride (N-benzyl-N—(C8-C18 alkyl)-N,N-dimethylammonium chloride), benzoxonium chloride or the like. Examples of other suitable preservatives include alkyl-mercury salts of thiosalicylic acid, such as, for example, thiomersal; phenylmercuric nitrate, phenylmercuric acetate or phenylmercuric borate; sodium perborate; sodium chlorite; parabens, such as, for example, methylparaben or propylparaben; alcohols, such as, for example, chlorobutanol, benzyl alcohol or phenyl ethanol; guanidine derivatives, such as, for example, chlorohexidine or polyhexamethylene biguanide; imidazolidinyl urea (Germall™) or sorbic acid. Preferred preservatives are quaternary ammonium compounds, in particular benzalkonium chloride or its derivative such as Polyquad (see U.S. Pat. No. 4,407,791), alkyl-mercury salts and parabens. Where appropriate, a sufficient amount of preservative is added to the ophthalmic composition to ensure protection against secondary contaminations during use caused by bacteria and fungi.

In another embodiment, the HA compositions for ophthalmic use do not include a preservative. Such compositions would be useful for patients who wear contact lenses, or those who use several topical ophthalmic drops and/or those with an already compromised ocular surface (e.g., dry eye) wherein limiting exposure to a preservative may be more desirable.

The HA compositions for ophthalmic use may additionally require the presence of a solubilizer, in particular if the active or the inactive ingredients tends to form a suspension or an emulsion. Solubilizers suitable for the hyaluronan compositions used in the methods of the invention include, for example, tyloxapol, fatty acid glycerol polyethylene glycol esters, fatty acid polyethylene glycol esters, polyethylene glycols, glycerol ethers, a cyclodextrin (for example alpha-, beta- or gamma-cyclodextrin, e.g. alkylated, hydroxyalkylated, carboxyalkylated or alkyloxycarbonyl-alkylated derivatives, or mono- or diglycosyl-alpha-, beta- or gamma-cyclodextrin, mono- or dimaltosyl-alpha-, beta- or gamma-cyclodextrin or panosyl-cyclodextrin), polysorbate 20, polysorbate 80 or mixtures of these compounds. A preferred solubilizer may be a reaction product of castor oil and ethylene oxide, for example the commercial products Cremophor EL® or Cremophor RH40®. Reaction products of castor oil and ethylene oxide have proved to be particularly good solubilizers that are tolerated extremely well by the eye. Another preferred solubilizer may be tyloxapol or cyclodextrin. The concentration used depends especially on the concentration of the hyaluronan in the composition. The amount added is typically sufficient to solubilize the hyaluronan in the composition. For example, the concentration of the solubilizer is from 0.1 to 5000 times the concentration of the hyaluronan in the composition.

The HA compositions for ophthalmic use may also comprise further non-toxic excipients, such as, for example, emulsifiers, wetting agents or fillers, such as, for example, the polyethylene glycols designated 200, 300, 400 and 600, or Carbowax designated 1000, 1500, 4000, 6000 and 10000. The amount and type of excipient added is in accordance with the particular requirements and is generally in the range of from approximately 0.0001 to approximately 90% by weight.

Other compounds may also be added to the formulations of the present invention to increase the viscosity of the carrier. Examples of viscosity enhancing agents include, but are not limited to, polysaccharides, such as chondroitin sulfate and its salts, dextrans, various polymers of the cellulose family; vinyl polymers; and acrylic acid polymers.

In one embodiment, the hyaluronan compositions intended for ophthalmic use, in addition to HA, may include additional ingredients that are typically found in ophthalmic compositions. Examples of such components may include other active ingredients, including, but not limited to, vasoconstrictors, antiallergenic agents, antiinfectives, steroids, anesthetics, anti-inflammatories, analgesics, dry eye agents (e.g., secretagogues, mucomimetics, polymers, lipids, antioxidants), or be administered in conjunction (simultaneously or sequentially) with compositions comprising other active ingredients, including, but not limited to, vasoconstrictors, antiallergenic agents, antiinfectives, steroids, anesthetics, anti-inflammatories, analgesics or dry eye agents (e.g., secretagogues, mucomimetics, polymers, lipids, antioxidants).

In some embodiments, the hyaluronan compositions of the inventions are administered to an ocular surface of a subject, such as under the eye lid, e.g., under the upper or lower eye lid, of the subject or at the cornea-eyelid interface of the subject. In some embodiments, the hyaluronan compositions of the invention are not suitable for use, or are not used, as a viscosurgical tool or a device during ophalmic surgery, i.e., are not suitable for injecting, or are not injected, into the eye during ocular surgery.

In one example, the hyaluronan compositions of the invention are administered to a subject immediately prior to rest or sleep.

VI. Hyaluronan Compositions for Skin Care/Dermatological Uses

The present invention also provides methods for alleviating pain and discomfort while minimizing at least one skin imperfection in a subject in need thereof by administering compositions comprising HA. Such HA compositions intended for skin care/dermatological use, in addition to HA, may include additional ingredients that are typically found in such compositions, e.g., compositions that are used as dermal fillers. Such ingredients may include, e.g., collagen, carnitine, Vitamin E, Vitamin A and chondroitin sulfate.

In some embodiments, an HA composition for skin care/dermatological use is injected into the skin. Accordingly, it may be formulated in the form of a container filled with a HA composition, e.g., a pre-filled syringe. Any pre-filled syringes known to one of skill in the art may be used in combination with a composition of the invention. Pre-filled syringes that may be used are described in, for example, in PCT Publications WO05032627, WO08094984, WO9945985, WO03077976, U.S. Pat. Nos. 6,792,743, 5,607,400, 5,893,842, 7,081,107, 7,041,087, 5,989,227, 6,807,797, 6,142,976, 5,899,889, US Patent Publications US20070161961A1, US20050075611A1, US20070092487A1, US20040267194A1 or US20060129108A1. Pre-filled syringes may be made of various materials. In one embodiment a pre-filled syringe is a glass syringe. In another embodiment a pre-filled syringe is a plastic syringe. One of skill in the art understands that the nature and/or quality of the materials used for manufacturing the syringe may influence the stability of an HA composition stored in the syringe. In one embodiment, a pre-filled syringe comprises a silicone-based lubricant. In one embodiment, a pre-filled syringe comprises baked-on silicone. In another embodiment, a pre-filled syringe is free from silicone-based lubricants. One of skill in the art also understands that small amounts of contaminating elements leaching into the formulation from the syringe barrel, syringe tip cap, plunger or stopper may also influence the stability of the composition. For example, it is understood that tungsten introduced during the manufacturing process may adversely affect formulation stability. In one embodiment, a pre-filled syringe may comprise tungsten at a level above 500 ppb. In another embodiment, a pre-filled syringe is a low tungsten syringe. In another embodiment, a pre-filled syringe may comprise tungsten at a level between about 500 ppb and about 10 ppb, between about 400 ppb and about 10 ppb, between about 300 ppb and about 10 ppb, between about 200 ppb and about 10 ppb, between about 100 ppb and about 10 ppb, between about 50 ppb and about 10 ppb, between about 25 ppb and about 10 ppb.

VII. Hyaluronan Compositions for Wound Healing

The present invention also provides methods for alleviating pain and discomfort while facilitating wound healing in a subject in need thereof. Such HA compositions intended for topical use, in addition to HA, may include additional ingredients that are typically found in such compositions. Such ingredients may include, e.g., 1,3-butylene glycol, glycerine, xanthan gum, sodium chondroitin sulfate, ethanol, methyl p-hydroxybenzoate, polyoxyethylene-polyoxypropylene, decyltetradecyl ether, sodium citrate, sodium edetate and vitamins, e.g., Vitamin A, Vitamin B, Vitamin C, Vitamin D, Vitamin E and Vitamin K. Such ingredients may also include additional pharmaceutically active substances. In some cases, these additional pharmaceutically active substances do not comprise analgesics for treating pain. In other cases, these pharmaceutically active substances comprise antibiotics, e.g., antibiotics that are typically used to treat skin infections and are intended for topical use.

The HA compositions for use in the methods disclosed herein also encompass a finished, packaged and labeled pharmaceutical product. This article of manufacture includes the appropriate unit dosage form in an appropriate vessel or container such as a glass vial, pre-filled syringe or other container that is hermetically sealed. In one embodiment, the unit dosage form is provided as a sterile particulate free HA composition that is suitable for parenteral administration, e.g., intra-dermal or sub-dermal administration to a subject, e.g., the face, neck, arms, legs, or back, of a subject.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question, as well as how and how frequently to administer the HA composition. In other words, the article of manufacture includes instruction means indicating or suggesting a dosing regimen including, but not limited to, actual doses, monitoring procedures, and other monitoring information.

VIII. Methods for Alleviating Pain and Discomfort Associated with Dry Eyes

Dry eye disease is an ocular disease affecting approximately 10-20% of the population. It may be associated with a pathological condition, such as cataract or an autoimmune disorder, or, in the absence of a pathological condition, may result under certain circumstances, such as such as prolonged visual tasking, working on a computer, being in a dry environment, contact lens use or exposure to medications that result in drying of the eye surface.

In individuals suffering from dry eye, the reflex that results in blinking and the secretion of supportive tear substances is compromised. Signs and symptoms of dry eye include ocular dryness; decreased tear production, volume, and flow; abnormal tear composition; increased tear osmolarity; keratitis, conjunctival and corneal staining; redness; blurry visions; decreased tear film break-up time; increased conjunctival redness; excess debris in tear film; ocular grittiness; ocular burning; foreign body sensation in the eye; excess tearing; photophobia; ocular stinging; refractive impairment; ocular sensitivity; ocular irritation and discomfort resulting from prolonged contact lens wear. The excess tearing response may seem counterintuitive, but it is a natural reflex response to the irritation and foreign body sensation caused by the dry eye. Some individuals may also experience ocular itching due to a combination of ocular allergy and dry eye symptoms.

There are many possible variables that also can influence a person's symptoms of dry eye, including levels of circulating hormones, various autoimmune diseases (e.g., Sjorgren's syndrome and systemic lupus erythematosus), ocular surgeries including PRK or LASIK, many medications, environmental conditions, visual tasking such as computer use, ocular fatigue, contact lens wear, and mechanical influences such as corneal sensitivity, partial lid closure, surface irregularities (e.g., pterygium), and lid irregularities (e.g., ptosis, entropion/ectropion, pinguecula). Environments with low humidity, e.g., those that cause dehydration, can exacerbate or cause dry eye symptoms, such as sitting in an aeroplane or a car with the defroster on or living in a dry climate zone. In addition, visual tasking can also exacerbate symptoms. Tasks that can greatly influence symptoms include watching TV or using a computer for long periods of time where the blink rate is decreased.

Compositions containing HA have been previously used for treating dry eye conditions. HA-containing eye drops are commercially available and typically contain HA at a concentration of less than 1%. Exemplary commercially available eye drops containing HA include Opticalm eye drops (0.2% HA); Aquify comfort drops (0.1% HA); Blink (0.15% HA); Hyal-drop (0.2% HA); Hycosan (0.1% HA); Oxyal (0.15% HA); and Vismed (0.18% and 0.8% HA).

Applicants have surprisingly discovered that highly concentrated HA compositions that comprise HA at a concentration of greater than about 30 mg/mL (or 3% HA), e.g., 40 mg/mL (or 4% HA) may be effectively administered to an eye of a subject for treating a dry eye condition. Such highly concentrated HA compositions have not been previously used for treating dry eyes, as it was considered that these compositions were too viscous to be administered to an eye effectively.

Applicants have also surprisingly discovered that, once administered to an eye, concentrated HA compositions are surprisingly effective at treating pain and discomfort associated with a dry eye condition. Without wishing to be bound by a specific theory, it is believed that pain associated with a dry eye condition may be modulated by TRPV1 channels of nociceptors, and that HA molecules in highly concentrated HA compositions interact with the TRPV1 channels present on ocular sensory nerves and corneal cells, thereby reducing the responsiveness of the nociceptors to noxious stimuli. Accordingly, in some embodiments, the pain and discomfort associated with a dry eye condition is modulated by receptor potential vanilloid subtype 1 (TRPV1) channels.

Moreover, the characteristic elastoviscous properties of the concentrated HA reduce the removal by normal tearing and blinking of the solution applied on the eye surface, thereby prolonging the protective effects of the HA solution.

The present invention provides a method for alleviating pain and discomfort associated with a dry eye condition in a subject in need thereof, comprising administering to an eye of the subject a composition comprising hyaluronan, wherein the hyaluronan is present in the composition at a concentration of greater than about 30 mg/mL; the hyaluronan has an average molecular weight of between about 1 and about 2 million; and the hyaluronan is not cross-linked and/or is substantially free of chemical modifications, thereby alleviating said pain and discomfort in said subject.

In some cases, the HA compositions intended for ophthalmic use are in the form a gel, an ointment, a liniment, a lotion or a cream. In certain aspects, this HA composition is not in the form of a lens or a microsphere.

The HA compositions intended for ophthalmic use may be administered to the ocular surface, such as under the eye lid e.g., under the upper or lower eye lid, or at the cornea-eyelid interface. In one aspect, the HA compositions are not injected into the eye of the subject. Because the subject's ability to see clearly may be compromised immediately after the administration of the HA compositions due to their high viscosity, these compositions may be administered to the eye of the subject immediately prior to rest or sleep.

One of ordinary skill in the art would be able to ascertain the appropriate administration schedule for the ophthalmic HA compositions described herein in order to achieve alleviation of pain and discomfort associated with a dry eye condition. For example, the HA compositions may be administered daily for about 3 days, 4 day, 5 days, 6 days, 1 week, 2 weeks, 3 weeks, 4 weeks, 1 month, 2 months, etc., or for any length of time until alleviation of pain and discomfort associated with a dry eye condition is achieved. In some embodiments, such alleviation of pain and discomfort may be alleviated for long term, e.g., lasting for about 12 hours, about 24 hours, about 1 day, about 3 days, about 5 days, about 7 days, about 14 days or about 28 days.

The term "dry eye condition" includes, but is not limited to, a dry eye condition associated with one or more symptoms selected from the group consisting of ocular dryness; decreased tear film break-up time; decreased tear production, volume, and flow; abnormal tear composition; increased tear osmolarity; keratitis; conjunctival and corneal staining; redness; blurry vision; increased conjunctival redness; excess debris in tear film, ocular grittiness; ocular burning; foreign body sensation in the eye; excess tearing; photophobia; ocular stinging; refractive impairment; ocular sensitivity; ocular irritation and discomfort resulting from prolonged contact lens wear.

The dry eye condition may also be associated with a condition selected from the group consisting of an autoimmune disorder; an ocular surgery; ingestion of a medication; dry environmental conditions; prolonged computer use; ocular fatigue; contact lens wear, corneal sensitivity; partial lid closure; surface irregularities; eye lid irregularities; and a condition associated with neuropathic pain, such as cataract or retinal detachment. In one example, the dry eye condition may be associated with an ocular surgery, such as photorefractive surgery, e.g., photorefractive keratectomy (PRK), cataract surgery, retinal detachment surgery, laser-assisted in situ keratomileusis (LASIK), or any corneal surgical procedure involving damage to corneal sensory nerves.

IX. Methods for Alleviating Pain and Discomfort while Minimizing Skin Imperfections HA is the major component of the extracellular matrix (ECM) and is present in particularly large quantities in the soft connective tissues, such as the skin. In normal skin, HA is mainly synthesized by dermal fibroblasts and epidermal keratinocytes. With its residues bearing a negative charge, HA functions as a water pump for maintaining the hydration and elasticity of the skin. The HA has a main role in controlling the distribution of food, hormones, vitamins and inorganic salts of the connective tissue and in cleaning metabolic waste which may induce inflammatory reactions. With age, the amount of HA and its degree of polymerization decreases, resulting in a decrease in the amount of water retained in the connective tissue. The skin is then subjected to an aging process which results in an increase of fibrosis and a decrease in the quality of elastic fibers.

HA has been widely used for cosmetic applications that include both the use of HA compositions in the form of creams or gels for topical applications and the use of HA compositions for injecting into the skin as dermal fillers. The latter use involves injecting HA compositions into the top skin layers of the a subject, e.g., the face, neck, arms, legs, torso or chest, of a subject. This use results in the reduction of wrinkles due to a mechanical filling effect of the cutaneous depression resulting from the wrinkle, and due to a preventive effect against skin aging and degradation of the ECM that is essential to maintaining the mechanical properties of the skin elasticity and firmness.

Although injection of dermal fillers for soft tissue augmentation is a minimally invasive dermatological procedure, patients often express concern about pain associated with such a procedure. Topical anesthetic creams are often used to alleviate pain during these procedures, and anesthetics are also included in the HA compositions used for injection.

The present invention obviates the need for an anesthetic use during these procedures. Specifically, the present invention provides methods for alleviating pain and discomfort associated with a dermatological procedure while minimizing at least one skin imperfection in a subject in need thereof by administering to the subject highly concentrated HA compositions. As explained above, it was surprisingly discovered that the highly concentrated HA compositions described herein are surprisingly effective at treating pain and discomfort associated with a dermatological procedure that may comprise, e.g., an injection into the skin of a subject. Without wishing to be bound by a specific theory, it is believed that pain associated with injecting HA compositions into the skin may be modulated by TRPV1 channels of nociceptors, and that HA molecules in highly concentrated HA compositions interact with the TRPV1 channels present in sensory nerves and epithelium and connective tissue cells of the skin and subcutaneous tissue, thereby reducing the responsiveness of the nociceptors to noxious stimuli.

In some embodiments, the HA compositions for cosmetic use may be administered to a subject in need thereof via an injection, e.g., subcutaneous or intradermal injection, using an injection device, such as a needle, a trocar, a cannula or a perfusion device. The injection device suitable for injecting the HA compositions of the invention may have a nominal diameter of 2.11 mm or greater (corresponding to 14G needle, or a needle gauge of 14 of greater). In some embodiments, the HA compositions of the invention may be too viscous for administration using smaller needles, e.g., needles having a nominal diameter of less than 2.11 mm. In other embodiments, the HA compositions of the invention may allow administration using smaller injection devices having a nominal diameter of less than 2.11 mm.

For example, a device suitable for injecting the HA compositions of the invention, such as a syringe, may have a nominal diameter of about 0.31 mm, 0.34 mm, 0.36 mm, 0.41 mm, 0.474 mm, 0.46 mm, 0.49 mm, 0.515 mm, 0.51 mm, 0.54 mm, 0.57 mm, 0.59 mm, 0.642 mm, 0.64 mm, 0.67 mm, 0.718 mm, 0.72 mm, 0.77 mm, 0.82 mm, 0.87 mm, 0.91 mm, about 0.99 mm, about 1.07 mm, about 1.17 mm, about 1.27 mm, about 1.42 mm, about 1.47 mm, about 1.57 mm, about 1.65 mm, about 1.73 mm, about 1.83 mm, about 1.98 mm, about 2.11 mm, about 2.26 mm, about 2.41 mm, about 2.54 mm or about 2.77 mm, corresponding, respectively, to gauge of 30, 29, 28, 27, 26 s, 26, 25.5, 25 s, 25, 24.5, 24, 23.5, 23 s, 23, 22.5, 22 s, 22, 21.5, 21, 20.5, 20, 19.5, 19, 18.5, 18, 17.5, 17, 16.5, 16, 15.5, 15, 14.5, 14, 13.5, 13, 12.5 or 12 (or 30 G, 29 G, 28 G, 27 G, 26 sG, 26 G, 25.5 G, 25 sG, 25 G, 24.5 G, 24 G, 23.5 G, 23 sG, 23 G, 22.5 G, 22 sG, 22 G, 21.5 G, 21 G, 20.5 G, 20 G, 19.5 G, 19 G, 18.5 G, 18 G, 17.5 G, 17 G, 16.5 G, 16 G, 15.5 G, 15 G, 14.5 G, 14 G, 13.5 G, 13 G, 12.5 G or 12 G needles). In one embodiment, the HA compositions of the invention may be administered using an 18G syringe needle having a nominal diameter of about 1.27 mm. In some embodiments, the HA compositions of the invention may be too viscous for administration using smaller needles, e.g., needles having a nominal diameter of less than 1.27 mm.

In some embodiments, the methods of the present invention may also comprise administering to a subject highly concentrated HA compositions in the form of an injectable implant, in particular, a dermal implant.

The compositions according to the invention are particularly intended for use in humans or animals in reconstructive or plastic surgery or cosmetic dermatology for filling wrinkles, fine lines, skin depressions, and scars, including the filling of skin depressions caused by lipodystrophy or lipoatrophy. The composition may be an implant as defined above.

X. Methods for Alleviating Pain and Discomfort while Facilitating Wound Healing

Skin provides a mechanical barrier to the external environment and acts to prevent the ingress of infectious agents. Once injured, the tissues beneath are exposed to infection; therefore, rapid and effective healing is of crucial significance to reconstruct a barrier function. Skin wound healing in adults is a complex process, and includes multiple stages, such as inflammation, granulation tissue formation, reepithelization and remodeling. HA likely plays a multifaceted role in mediation of these cellular and matrix events. Often, topical anesthetics are administered to wounds in order to alleviate pain associated with these wounds.

The present invention provides methods for effectively treating skin wounds while simultaneously providing pain relief and obviating the need for a topical anesthetic use. Specifically, the present invention provides methods for alleviating pain and discomfort while facilitating wound healing, by administering to a subject in need thereof highly concentrated HA compositions. As explained above, it was surprisingly found that the highly concentrated HA compositions described herein are surprisingly effective at treating pain and discomfort associated with wound healing. Without wishing to be bound by a specific theory, it is believed that pain associated with injecting HA compositions into the skin may be modulated by TRPV1 channels of nociceptors, and that HA molecules in highly concentrated HA compositions interact with the TRPV1 channels present in the sensory nerves innervating the wounded area and in connective tissue cells of this area, thereby reducing the responsiveness of the nociceptors to noxious stimuli.

In accordance with the methods of the invention, the highly concentrated HA compositions intended for topical administration to skin wounds may be administered topically on the surface of a wound or a scar on the skin. The compositions may be in the form of aqueous gels or polyalcohols containing thickening polymers such as cellulose derivatives or acrylic polymers, together with other excipients in conventional use, such as preservatives, perfumes and the like.

A treatment, preventive or alleviating effect is evident when there is a statistically significant improvement in one or more parameters of disease status or a pathological condition, e.g., pain and discomfort associated with a dry eye condition, a skin care/dermatological procedure or a healing wound. A treatment, or alleviating or preventive effect is also evident by a failure to worsen or to develop symptoms where they would otherwise be anticipated. As an example, a favorable change of at least 10% in a measurable parameter of disease or condition, e.g., pain and discomfort, and, preferably at least 20%, 30%, 40%, 50% or more can be indicative of effective treatment. The term "prevent" or "preventing", as used herein, comprises, e.g., prevention of re-occurrence of pain and discomfort in a subject who has previously experienced the pain.

In some embodiments, the subject is a human, a mammal, e.g., a domestic animal (such as a cat or a dog), a farm animal (such as a cow, a sheep, a horse, a donkey), or a rodent (such as a guinea pig, a mouse or a rat). In a specific embodiment, the subject is a human. In another specific embodiment, the subject is a dog.

As used herein, the term "reducing at least one symptom" comprises diminishing, ameliorating or eliminating at least one symptom associated with pain and discomfort. This term also comprises reducing the extent of the activation of ion channels, such as TRPV1 channels, that are involved in the process of pain transduction in neurons, upon administration of an HA composition of the invention. Activation of such channels may be measured, e.g., by measuring the change in intracellular Ca' in neurons after a nociceptive impulse, or by measuring whole-cell currents in neurons, upon administering an HA composition of the invention. Furthermore, the term "reducing at least one symptom" also comprises diminishing nociceptive firing of neurons upon administration of an HA composition of the invention.

In some embodiments, the methods of reducing pain and discomfort associated with dry eye condition, a skin care/dermatological procedure or a healing wound, comprise administering to a subject in need thereof a therapeutically effective amount of a composition of the invention. The term "therapeutically effective amount", as used herein, is intended to include an amount of an HA composition of the invention that, when administered to a subject in need thereof, is sufficient to treat, prevent, reduce or alleviate pain and discomfort. One of ordinary skill in the art, e.g., a physician, would be able to easily ascertain the amount of HA composition that would be therapeutically effective. In general, a therapeutically effective amount of the composition is between about 0.1 to about 500 mg, e.g., about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg.

A variety of treatment regimens are encompassed by the methods disclosed herein. For instance, a subject may receive a first dose of the HA compositions disclosed herein followed by additional doses. In some embodiments, a first dose is administered followed by a second dose at a specific interval. In some embodiments, the second dose is administered about 30 days, about 60 days, about 90 days, about 120 days, about 150 days, about 180 days, about 210 days, about 240 days, about 270 days, about 300 days, about 330 days, or about 360 days after the first dose. It should be appreciated that the dose regime may be adjusted based on the reduction in pain and discomfort experienced by the subject. In some embodiments, the subject will receive a dose every month, every two months, every three months, every four months, every five months, every six months, every seven months, every eight months, every nine months, every ten months, every eleven months, or every twelve months.

The present invention is further illustrated by the following Examples, which in no way should be construed as further limiting. The entire contents of all of the references (including literature references, issued patents, published patent applications, and co-pending patent applications) cited throughout this application are hereby expressly incorporated herein by reference.

EXAMPLES

Unless provided otherwise, the hyaluronan (HA) used in the compositions described herein is obtained from animal, human or bacterial sources. Unless provided otherwise, the compositions used herein are in physiological buffers.

Example 1. Reduction of Impulse Activity in Corneal Sensory Nerve Fibers by Topical Application of 4% Sodium Hyaluronan on the Cornea Excitation of nociceptors is the first step in the production of pain sensations. For acute pain, the magnitude of pain sensation correlates well with the firing frequency of nociceptive fibers and with the number of fibers recruited by the stimulus (Acosta et al., 2001, *J. Physiol.* 534(2), 511-525). Also, sustained pain after peripheral injury is associated with ongoing activity in nociceptors (Belmonte et al., 2004, *Ocular Surface*, 2, 248-253). Augmented sensory nerve impulse activity in corneal nerves is the first step in the generation of ocular discomfort and pain sensations. In the ocular surface, noxious stimuli are detected by polymodal nociceptor and mechano-nociceptor innervating the cornea and conjunctiva (Belmonte & Giraldez, 1981, *J. Physiol.*, 437, 709-725; Gallar et al., 1993, *J. Physiol.*, 468, 609-622). When inflammation occurs, polymodal nociceptors become sensitized and fire continuously, evoking sustained pain sensations. On the other hand, activity in corneal cold thermoreceptors has been associated with ocular surface evaporation and possibly also contributes to conscious sensations of ocular surface dryness (Gallar et al., 1993, *J. Physiol.*, 468, 609-622; Parra et al., 2010, *Nature Medicine*, 16, 1396-1399; Kovacs et al., 2016, *Pain*, 157, 399-417).

The objective of the experiments described below was to test the ability of hyaluronan at a concentration of 4% (4% HA) with an average molecular weight of 1-2 million to modify the spontaneous and stimulus-evoked nerve impulse discharges in sensory receptor fibers (mechano-nociceptors, polymodal nociceptors, cold thermoreceptors) innervating the cornea of guinea pigs.

An effective means of producing a chemical stimulation of corneal polymodal nociceptors is application of 98.5% $CO_2$, due to acidification elicited by local formation of carbonic acid (Chen et al., 1995, *Eur. J. Neurosci.* 7, 1154-1163). It has been proven that application of a similar pulse of $CO_2$ to the human cornea evokes in all instances an immediate and sharp sensation of pain (Chen et al., 1995, *Eur. J. Neurosci.* 7, 1154-1163; Acosta et al., 2001, *J. Physiol.* 534(2), 511-525). Because protons are formed rapidly in the surroundings of nerve terminals, the stimulating effect of $H^+$ is presumably direct and occurs through activation of a proton-gated ionic channel that depolarizes the nerve, possibly the 'capsaicin channel' TRPV1 and/or ASIC channels. Moreover, a decrease of the intracellular pH in epithelial cells of the cornea subjected to $CO_2$ stimulation may also lead to formation and release of inflammatory mediators (for instance, prostaglandins), which may sensitize corneal polymodal nociceptors, causing background discharge and enhanced impulse responses to direct acidic stimulation.

In the case of corneal cold thermoreceptors, these fibers exhibit a background, regular impulse activity at the basal corneal temperature of 34° C. and increase their firing frequency with very small temperature reductions, e.g., those occurring during tear evaporation (Belmonte et al., 2015, *Curr. Ophthalmol. Rep.* 3, 111-121).

Methods

Dunkin Hartley guinea pigs of both sexes weighing 200-300 g were used in the experiments. The study was carried out in accordance with the *NIH Guide for the Care and Use of Laboratory Animals* and the European Union Directive (2010/63/EU) and the Spanish regulations on the protection of animals used for research, and followed a protocol approved and supervised by the Ethics Committees of the University Miguel Hernandez.

Electrophysiological Recordings

The impulse activity of different functional types of peripheral corneal receptors was recorded. For this purpose, animals were euthanized with an intraperitoneal injection of 100 mg/kg sodium pentobarbitone, and both eyes were immediately enucleated together with the bulbar and tarsal conjunctiva and the optic and ciliary nerves, and placed in cold saline (4° C.).

Connective tissue and extraocular muscles were carefully removed from the excised eyeball to expose the back of the eye with the ciliary nerves around the optic nerve. The eye was then placed in a double chamber specially designed to keep the anterior segment of the eye with the conjunctiva separated from the back pole and the ciliary nerves. In the front part of the chamber, the conjunctiva was pinned to the separating wall in order to isolate both compartments, which were perfused separately. The anterior compartment was perfused with warm (34° C.) saline, dropping continuously over the upper corneoscleral border. In the rear compartment of the chamber filled with warmed mineral oil, nerve filaments were teased apart from the ciliary nerves and placed on an Ag—AgCl electrode for monopolar recording of single unit impulse activity using conventional electrophysiological equipment. Electrical signals were recorded with respect to an Ag/AgCl pellet in the posterior compartment. Electrical signals were transferred to a PC with a CED interface and analyzed with the appropriate software. Spontaneous activity of the selected unit was recorded for 1 minute before any intended stimulation. Mechanical threshold was determined thereafter using calibrated von Frey hairs (range 0.25-4.00 mN). Receptive fields of corneal afferent fibers were localized using mechanical stimulation with a fine paint brush and mapped afterwards using a suprathreshold von Frey hair. For chemical stimulation, a gas jet containing 98.5% $CO_2$ was applied on the corneal receptive field during 30 seconds. Thermal stimulation was performed by cooling (down to 20° C.) the perfusion solution by means of a custom-made Peltier device.

Data Analysis

In single fiber recordings of polymodal fibers, impulse firing of individual units discriminated accordingly to their stimulus modality, amplitude and shape was analyzed. Ongoing impulse activity was expressed as mean impulse frequency (in impulses/s) measured during 30 seconds at the beginning of the recording and during the interstimulus periods. Responses to $CO_2$ were quantified measuring the following parameters: latency: time delay between onset of the $CO_2$ pulse and the first impulse given by the unit; mean discharge rate: mean number of impulses per second (imp/s) throughout the $CO_2$ pulse; postdischarge: mean firing frequency (imp/s) during 30 seconds immediately after the $CO_2$ pulse.

In cold nerve fiber recordings, the following additional firing pattern parameters were calculated: mean firing frequency: average number of impulses recorded per second (impulses/s); cooling threshold: temperature during the cooling ramp at which a 25% increase of the mean nerve impulse frequency at basal temperature was obtained; peak response: maximal impulse/s value of the impulse frequency during the cooling ramp; temperature at the peak response: temperature value (° C.) at which peak frequency was reached.

Experimental Protocol

The following experimental sequence was followed:

Identification of Polymodal Nociceptive Fibers

A filament containing fibers innervating the cornea and responding to mechanical stimulation with a wet, fine brush applied to the corneal surface was identified. After splitting of the nerve filament, localization of a single corneal nociceptive unit was made by mechanical stimulation. For further characterization (determination of polymodality) of each isolated single unit, the following routine was performed:

1. mapping of the receptive field borders and determination of mechanical threshold with the von Frey filaments;

2. measuring a response to a 30 second pulse of 98.5% $CO_2$. If no response was detected, a new fiber was investigated.

Effect of 4% HA on Polymodal Nociceptors

A 4% HA solution was applied onto the corneal surface. The cornea regularly received a drop of saline to maintain humidity. After 4% HA instillation, a 30-second $CO_2$ pulse was applied onto the corneal surface at successive times (5, 20, 35, 50, 65 and 80 min after 4% HA application). The cornea was then washed continuously for 5 minutes with saline and the response to $CO_2$ measured 15 minutes and 20 minutes after washing. Electrical threshold was measured at the end of the protocol to confirm responsiveness of the fiber. The presence of spontaneous activity throughout the complete experimental procedure and the magnitude of the impulse response to the $CO_2$ stimuli were measured.

Identification of Cold Thermosensitive Fibers

A filament containing cold thermosensitive fibers innervating the cornea was identified by applying a drop of cold saline on the cornea. After splitting of the fiber, localization of the filament containing a single corneal cold unit was made using an ice-cooled metal bar (tip diameter 1 mm diameter) applied onto the cornea to map the receptive field.

Ongoing impulse activity exhibited by a single cold-sensitive nerve terminal at 34° C. was recorded. Cooling ramps from 34° C. to 15° C. were performed by changing the temperature of the receptive field with a Peltier device.

Effect of 4% HA on Cold Thermoreceptor Nerve Activity

A 4% HA was applied onto the ocular surface exposed in the front compartment of the chamber, and the effect on the cold thermoreceptor ongoing activity at 34° C. and on the response to cooling ramps was explored 5, 20, 35, 50, 65 and 80 minutes after HA application, as well as 15 and 20 minutes after washing the cornea.

The mean ongoing activity at the resting temperature of 34° C., the thermal threshold and the increase in nerve impulse activity during the cooling ramps were determined.

Results

In the intact cornea, sensory afferents identified as polymodal nociceptor fibers presented corneal receptive fields usually extending up to 1 mm into the adjacent sclera. The polymodal nociceptor fibers were silent at rest, responding to mechanical stimulation and also to a 98.5% $CO_2$.

The effects of 4% HA on the ongoing activity and the firing response to $CO_2$ were measured in 2 single polymodal and 2 cold sensitive units. The effects of $CO_2$ were analyzed before and after application of 4% HA on the corneal surface. As shown in Table 1 below, polymodal nociceptors were silent at rest, with no ongoing activity during a 2-minute recording period. They responded in about 2.5 seconds to a 30 second $CO_2$ pulse with a mean frequency of the impulse discharge of about 6 impulses per second. During the first 35 minutes after applying 4% HA onto the cornea, the response to $CO_2$ appeared markedly decreased and ceased afterwards. Washing after 80 minutes of 4% HA treatment gradually recovered the response to $CO_2$.

The impulse activity in cold thermoreceptor fibers, which represent about 10% of all corneal sensory afferents, was also recorded. We confirmed their regular ongoing impulse activity at 34° C. in intact eyes and the marked frequency increase caused by 15° C. cooling pulses, characteristic of ocular cold thermoreceptors (Gallar et al., 1993, *J. Physiol.*, 468, 609-622; Parra et al., 2010, *Nature Medicine*, 16, 1396-1399).

As shown in Table 1, exposure of the cornea for 4 hours to 4% HA decreased the background ongoing activity of cold thermoreceptors at 34° C. No clear changes in cold threshold were noticed but, as also shown in Table 1, the response to cold ramps was markedly decreased and only partially recovered 20 minutes after washing, while the peak frequency value evoked by the cold ramp returned to a normal value during this time.

Altogether, these results indicate that 4% HA reduces the abnormal impulse activity in polymodal nociceptor fibers resulting from acidic stimulation of cornea. This is possibly the result of an interaction of HA molecules with the TRPV1 channels of sensitized nociceptive nerve terminals (Caires et al., 2015, *Nat. Comm.* 6, 8095), evidencing that high concentrations of HA are very effective at eliciting this effect. Also, activity in cold thermoreceptors was diminished, possibly due to a more effective shielding of the corneal surface than HA solutions of lower concentrations.

Example 2. Force Requirements for Ejection of HA Through Various Needle Sizes

The pressure required to eject a 4% HA composition from a 3 mL syringe with needles of different diameter (30-18 G) has been measured and is shown in FIG. 1. Force was exerted by one plate of a two-plate balance, acting perpendicularly on the embolus of the syringe. Weights of increasing magnitude were added to the contralateral plate. As demonstrated by the results shown in FIG. 1, the HA compositions of the invention can be administered to subjects using needles with diameters of 30-18G.

TABLE 1

| | POLYMODAL NOCICEPTORS | | | | COLD THERMORECEPTORS | | | |
| | | | | | | Cooling | | |
| | Ongoing Activity | Latency | $CO_2$ response | Post-discharge | Spontaneous activity | Threshold | ramp response | Peak frequency | Temp. at peak |
|---|---|---|---|---|---|---|---|---|---|
| | | | | CONTROL | | | | | |
| | 0 | 2.4 ± 3.3 | 5.8 ± 4.1 | 1.3 ± 0.8 | 0.3 | 17.8 | 3.3 | 5.0 | 17.4 |
| | | | | 4% HA | | | | | |
| 5 min | 0 | 0 | 0 | 0 | 0 | 16.0 | 0.5 | 3.0 | 15.7 |
| 20 min | 0 | 9.6 ± 0 | 0.03 ± 0.04 | 0.02 ± 0.02 | 0 | 18.7 | 1.2 | 4.0 | 15.7 |
| 35 min | 0 | 23.9 ± 7.2 | 0.3 ± 0.2 | 0.6 ± 0.02 | 0 | 20.7 | 0.4 | 2.0 | 17.8 |
| 50 min | 0 | 0 | 0 | 0 | 0.8 | 16.9 | 1.2 | 3.0 | 16.6 |
| 65 min | 0 | 0 | 0 | 0 | 0.2 | n.r. | n.r. | n.r. | n.r. |
| 80 min | 0 | 0 | 0 | 0 | 0.3 | 15.8 | 0.5 | 1.0 | 15.8 |
| | | | | WASH | | | | | |
| 15 min | 0 | 8.4 ± 6.4 | 0.4 ± 0.1 | 0.8 ± 0.2 | 0.15 | 18.2 | 1.1 | 4.0 | 18.0 |
| 20 min | 0 | 14.8 ± 5.8 | 4.5 ± 3.2 | 3.1 ± 1.9 | 0.0 | 21.0 | 1.5 | 8.0 | 17.3 |

Ongoing activity, CO2 responses and postdischarges values of corneal polymodal nociceptors are expressed in impulses per second; latency in seconds.
For cold thermoreceptors, spontaneous activity, cooling ramp responses and peak frequency values were expressed in impulses per second.
Threshold and temperature at the peak frequency, in ° C; n.r.: impulse activity, absent.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method for alleviating pain and discomfort associated with minimizing at least one skin imperfection in a subject in need thereof, the method comprising administering to said subject a composition comprising hyaluronan, wherein:
   the hyaluronan is present in said composition at a concentration of greater than about 30 mg/mL;
   the hyaluronan has an average molecular weight of between about 1 and about 2 million;
   the hyaluronan is not cross-linked and/or is free of chemical modifications; and
   wherein the composition is free of a local anesthetic, thereby alleviating said pain and minimizing said at least one skin imperfection.

2. The method of claim 1, wherein hyaluronan is present in said composition at a concentration of about 40 mg/mL to about 60 mg/mL.

3. The method of claim 1, wherein hyaluronan is present in said composition at a concentration of about 40 mg/mL.

4. The method of claim 1, wherein the composition further comprises a buffer.

5. The method of claim 4, wherein the buffer is phosphate buffered saline (PBS).

6. The method of claim 1, wherein the composition has an elasticity of at least about 200 Pascal when measured at a frequency of 0.5 Hz.

7. The method of claim 1, wherein the composition has an elasticity of at least about 1,000 Pascal when measured at a frequency of 0.5 Hz.

8. The method of claim 1, wherein the composition has an elasticity of at least about 2,000 Pascal when measured at a frequency of 0.5 Hz.

9. The method of claim 1, wherein the composition has an elasticity of at least about 4,000 Pascal when measured at a frequency of 0.5 Hz.

10. The method of claim 1, wherein the composition is sterile.

11. The method of claim 1, wherein said composition is administered by an injection into the skin of said subject.

12. The method of claim 11, wherein said composition is injected into a region of the subject selected from the group consisting of the face, the neck, the arms, the legs, the torso and the chest of the subject.

13. The method of claim 12, wherein said composition is injected into the region selected from the group consisting of nasolabial region, upper lip region, forehead, eye region and cheek region.

14. The method of claim 11, wherein the composition is administered by an injection using a pre-filled syringe.

15. The method of claim 14, wherein the pre-filled syringe is a 1, 2, 3, 4, 5, 6, 7, 8, 9 or 10-mL pre-filled syringe.

16. The method of claim 15, wherein the pre-filled syringe is sterilized.

* * * * *

UNITED STATES PATENT AND TRADEMARK OFFICE
CERTIFICATE OF CORRECTION

| | |
|---|---|
| PATENT NO. | : 11,583,549 B2 |
| APPLICATION NO. | : 17/115242 |
| DATED | : February 21, 2023 |
| INVENTOR(S) | : Belmonte et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 7 days.

Signed and Sealed this
Twentieth Day of May, 2025

Coke Morgan Stewart
*Acting Director of the United States Patent and Trademark Office*